US005553622A

United States Patent [19]

McKown et al.

[11] Patent Number: 5,553,622

[45] Date of Patent: Sep. 10, 1996

[54] SYSTEM AND METHOD FOR CONTROLLING THE TEMPERATURE OF A CATHETER-MOUNTED HEATER

[76] Inventors: Russell C. McKown, 9696 Walnut, No. 1517, Dallas, Tex. 75243; Michael D. Quinn, 3121 Amesbury Dr., Plano, Tex. 75093; Mark L. Yelderman, 5205 Terrace View, Plano, Tex. 75093

[21] Appl. No.: 334,443

[22] Filed: Nov. 4, 1994

Related U.S. Application Data

[63] Continuation of Ser. No. 833,013, Feb. 10, 1992, abandoned, which is a continuation-in-part of Ser. No. 647,578, Jan. 29, 1991, abandoned.

[51] Int. Cl.⁶ ................................................. A61B 05/00
[52] U.S. Cl. ........................... 128/692; 128/713; 128/736
[58] Field of Search ................................. 128/691, 692, 128/713, 736; 219/497; 374/163, 185

[56] References Cited

U.S. PATENT DOCUMENTS

| | | | |
|---|---|---|---|
| 3,075,515 | 1/1963 | Richards | 128/692 |
| 3,359,974 | 12/1967 | Khalil | 128/713 |
| 4,089,336 | 5/1978 | Cage et al. | 128/303.1 |
| 4,091,813 | 5/1978 | Shaw et al. | 128/303.14 |
| 4,185,632 | 1/1980 | Shaw | 128/303.1 |
| 4,198,957 | 4/1980 | Cage et al. | 128/1 |
| 4,206,759 | 6/1980 | Shaw | 128/303.1 |
| 4,207,896 | 6/1980 | Shaw | 128/303.1 |
| 4,209,017 | 6/1980 | Shaw | 128/303.1 |
| 4,240,441 | 12/1980 | Khalil | 128/700 |
| 4,364,390 | 12/1982 | Shaw | 128/303.1 |
| 4,399,823 | 8/1993 | Donnelly | 374/163 |
| 4,507,974 | 4/1985 | Yelderman | 73/861.06 |
| 4,523,084 | 6/1985 | Tamura et al. | |
| 4,524,264 | 6/1985 | Takeuchi et al. | 219/497 |
| 4,549,073 | 10/1985 | Tamura et al. | |
| 4,572,206 | 2/1986 | Geddes et al. | 128/692 |
| 4,576,182 | 3/1986 | Normann | 128/736 |
| 4,671,295 | 6/1987 | Abrams et al. | 128/663 |
| 4,700,708 | 10/1987 | New et al. | 128/633 |
| 4,718,423 | 1/1988 | Willis et al. | 128/634 |
| 4,722,347 | 2/1988 | Abrams et al. | 128/663 |
| 4,733,669 | 3/1988 | Segal | 128/663 |

(List continued on next page.)

FOREIGN PATENT DOCUMENTS

WO91/03208 3/1991 European Pat. Off. .

OTHER PUBLICATIONS

A Continuous Cardiac Output Computer Based On Thermodilution Principles, R. A. Normann et al., Annals of Biomedical Eng., vol. 17, pp. 61–73, 1989.

Investigation Of A Continuous Heating Cooling Technique For Cardiac Output Measurement, Kevin C. Ehlers et al., Annals of Biomedical Eng., vol. 15, pp. 551–565, 1987.

(List continued on next page.)

*Primary Examiner*—Angela D. Sykes
*Assistant Examiner*—Robert L. Nasser, Jr.
*Attorney, Agent, or Firm*—Oblon, Spivak, McClelland, Maier & Neustadt, P.C.

[57] ABSTRACT

A system for keeping the surface temperature of an electric resistance-type heater element in a thermodilution catheter within safe physiological limits includes, in the preferred embodiment, a heater element core temperature monitor, a monitor for monitoring the power that is supplied to the heater element, and a surface temperature calculator for calculating the surface temperature of the heater element based on the core temperature, supplied power, and information representing the characteristics of the particular catheter under anticipated clinical conditions. A second aspect of the invention involves a system for determining the supply of power to the heater element based on the core temperature of the heater element. A third aspect of the invention involves is a system readiness test for determining, in vivo, that the thermodilution catheter system is properly calibrated before the system is operational. Methods of operation for each of the above-referenced aspects of the invention are also disclosed.

23 Claims, 10 Drawing Sheets

U.S. PATENT DOCUMENTS

| | | | |
|---|---|---|---|
| 4,759,378 | 7/1988 | Swendson et al. | 128/786 |
| 4,819,655 | 4/1989 | Webler | 128/713 |
| 4,832,504 | 5/1989 | Hori et al. | 374/163 |
| 4,941,475 | 7/1990 | Williams | 128/692 |
| 4,947,852 | 8/1990 | Nassi et al. | 128/662.06 |
| 4,951,682 | 8/1990 | Petre | 128/713 |
| 5,047,025 | 9/1991 | Taylor et al. | 606/31 |
| 5,214,267 | 5/1993 | Hoshi et al. | 219/497 |
| 5,277,191 | 1/1994 | Hughes | 128/713 |

OTHER PUBLICATIONS

Cardiac Output Estimation By A Thermodilution Method Involving Intravascular Heating And Thermistor Recording, T. Barankay et al., Acta Physiologica Acadimiae Scientiarum Hungaricae, Tomus 38 (2–3), pp. 167–173, 1970.

Measurement Of Cardiac Output By Thermal–Dilution And Direct Fick Methods In Dogs, H. H. Khalil et al., Journal of Appl. Physiol., vol. 21 (3), pp. 1131–1135 1966.

Determination Of Cardiac Output In Man By A New Method Based On Thermodilution, H. H. Khalil et al., Preliminary Communications, Jun. 22, 1963, pp. 1352–1354.

Repeated Or Continual Measurements Of Cardiac Output In The Squirrel Monkey (*Saimiri sciureus*) By Thermodilution, H. H. Khalil, Bureau of Med. and Surgery, MR011.01.4, Naval Aerospace Med. Inst., Mar. 8, 1968.

CRC Handbook Of Chemistry And Physics, 60th Ed., 1979–1980, p. E-85 Cole–Parmer Instrument Co., Niles, Il, (Catalog p. 1259–1261).

Baxter Healthcare Corp., (Catalog pp. 1, 2, 5 and 6) Jun. 1992 Service Manual For COM–1 Thermodilution Cardiac Output Computer, American Edwards Laboratories, Jun. 1884, p. 6, Table 2.1.

Continuous Thermal Measurement Of Cardiac Output, IEEE Transactions On Biomedical Eng., vol. BME–31, No. 5, May 5, 1984.

Abrams et al, "Transtracheal Doppler: A New Procedure for Continuous Cardiac Output Measurement", Anesthesiology, vol. 70, No. 1, pp. 134–138, Jan. 1989.

Fegler, G. A. "Measurement of Cardiac Output in an Aesthetized Animals by a Thermo–Dilution Method", Quarterly Journal of Experimental Physiology, 1954, vol. 39, pp. 153–154.

Gibbs, "A Thermoelectric Blood Flow Recorder in the Form of a Needle", 1933, vol. 41, pp. 141–146.

Ham et al., "Studies in Destruction of Red Blood Cells, Chapter IV. Thermal Injury", *Blood*, vol. 3, pp. 373–403 (1948).

Morris et al., "Thin Film Thermistors", Journal of Physics Engineering; Scientific Instruments, 1975, vol. 8, pp. 411–414.

Ponder, "Shape and Transformations of Heated Human Red Cells", *J. Exp. Biol.*, vol. 26, pp. 35–45 (1950).

Segal, "Instantaneous and Continuous Cardiac Output Obtained With a Doppler Pulmonary Artery Catheter, Journal of the American College of Cardiology", vol. 13, No. 6, May 1989, pp. 1382–1392.

Stewart, G. N., "The Output of the Heart in Dogs", The American Journal of Physiology, vol. 57, pp. 27–50, 1921.

Williamson et al., "The Influence of Temperature on Red Cell Deformability", *Blood*, vol. 46, pp. 611–624 (1975).

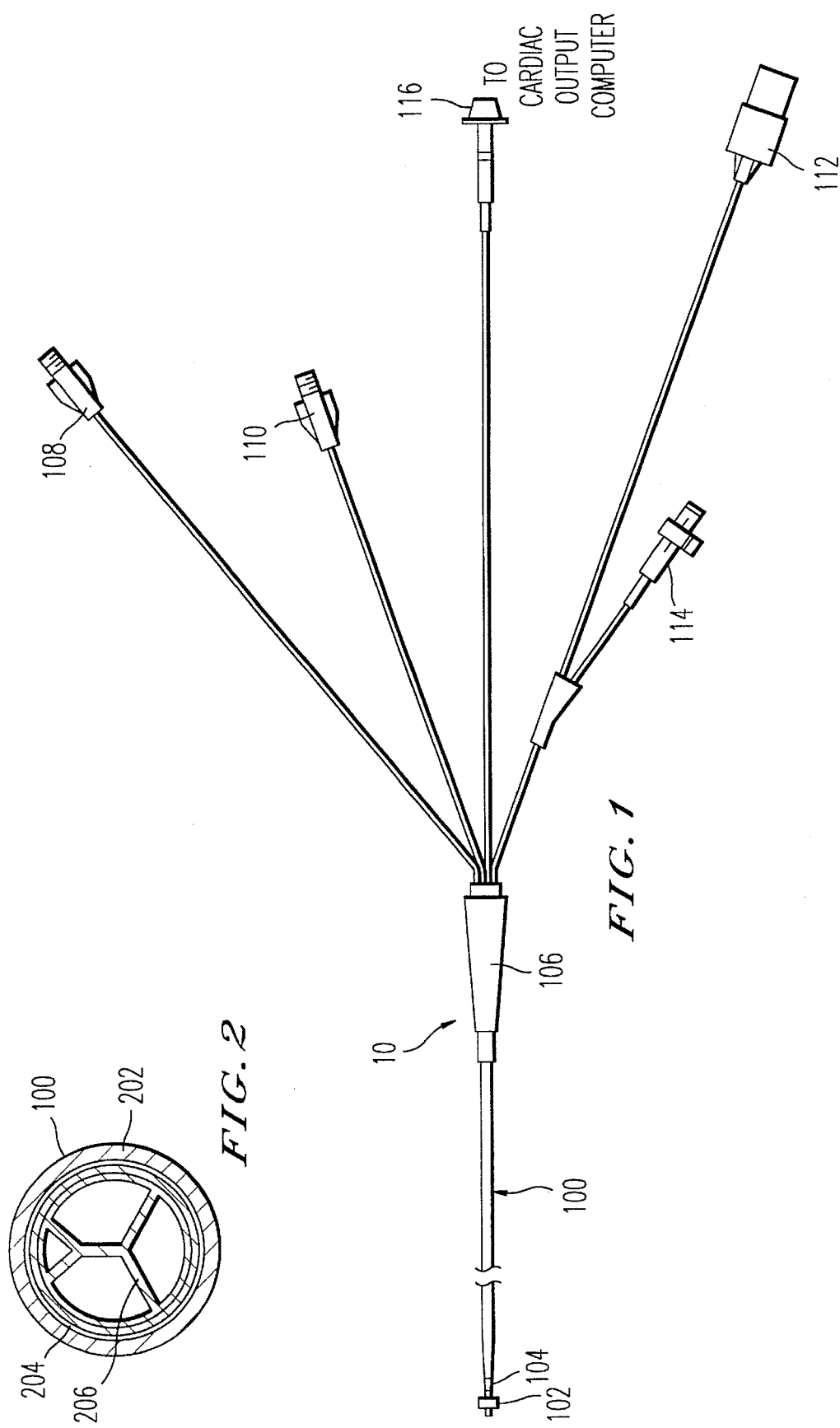

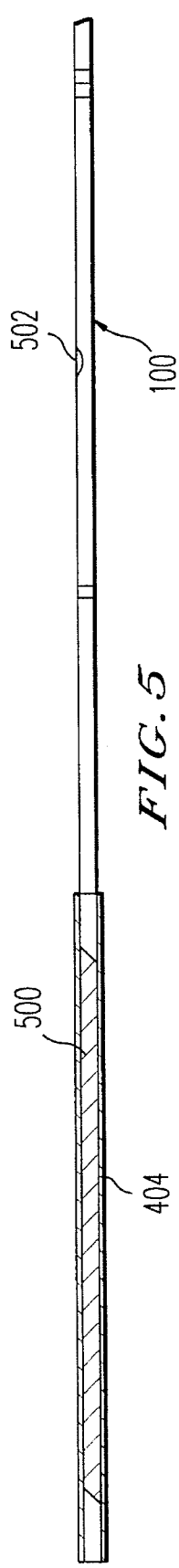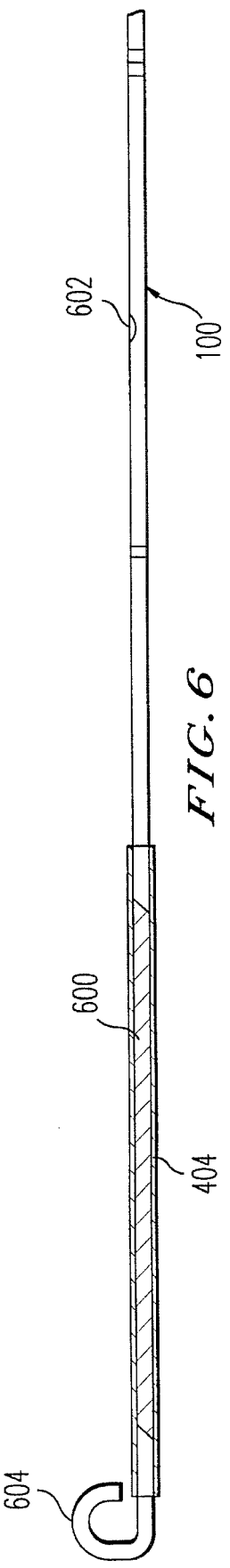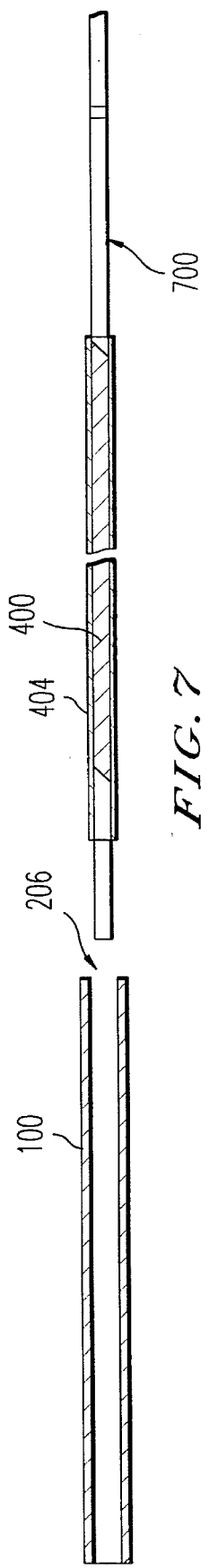

SYSTEM AND METHOD FOR CONTROLLING THE TEMPERATURE OF A CATHETER-MOUNTED HEATER

CROSS-REFERENCE TO RELATED APPLICATIONS

This application is a continuation of application Ser. No. 07/833,013 filed Feb. 10, 1992, now abandoned, which is a continuation-in-part of application Ser. No. 07/647,578 filed Jan. 29, 1991, also abandoned.

BACKGROUND OF THE INVENTION

1. Field of the Invention

This invention relates generally to thermodilution catheters of the type that have an electric resistance-type heating element for applying heat to a patient's blood for purposes of measuring a physiological condition, such as volumetric blood flow. More specifically, the invention relates to systems and methods for maintaining the surface temperature of such a heating element at a level which will not be harmful to a patient.

2. Description of the Prior Art

Catheters have long been used for applying therapeutic or diagnostic preparations directly into the blood stream of animals or humans. Catheters are also commonly used to measure such parameters as cardiac output, blood pressure, blood volume, blood components and the like.

Numerous techniques have been disclosed in the prior art for measuring blood flow using catheters. Once such technique, termed indicator dilution, relies on the introduction of a marker into the bloodstream, the theory being that the marker will dissipate at a rate which is a function of blood flow as measured in units of volume per unit of time.

The present inventors believe, clinically, that heat is the preferred marker for such an indicator dilution system. Unlike other indicators, heat is conserved in the immediate vascular system, but is largely dissipated in the periphery in one circulation time so as to eliminate recirculation and accumulation problems. Cold (negative heat) is an indicator which can also be used very effectively in a clinical setting. Large amounts of cold may be used, for cold has relatively no deleterious effects on blood and surrounding tissues. However, a disadvantage of cold as an indicator is that it must be supplied in a chilled fluid carrier such as saline, because cold producing transducers are not commercially available. Cold-based indicator systems are disclosed in U.S. Pat. No. 4,819,655 to Webler and in U.S. Pat. No. 4,941,475 to Williams. Both of those systems have significant clinical limitations in that the circulating fluid must be cooled to near ice temperature prior to input into the catheter and temperature equilibrium must be established, which takes a significant amount of time. In addition, the enlarged catheter segment which is necessary for containing the cooling elements may restrict blood flow.

A disadvantage of heat as an indicator is that even small increases in heat transducer temperature can have a deleterious effect on blood and local tissue. In fact, it can be inferred from the teachings of Ham et al. in "Studies in Destruction of Red Blood Cells, Chapter IV Thermal Injury" Blood, Vol. 3, pp. 373–403 (1948), by Ponder in "Shape and Transformations of Heated Human Red Cells", *J. Exp. Biol.*, Vol. 26, pp. 35–45 (1950) and by Williamson et al. in "The Influence of Temperature on Red Cell Deformability", *Blood*, Vol. 46, pp. 611–624 (1975), that a maximum safe filament surface temperature is probably about 48° C.

A heater element in a catheter must satisfy several requirements if it is to be used clinically. Most importantly, the heat transducer or filament must be electrically safe. It also must only minimally increase the catheter cross-sectional area or diameter of the catheter and must be made of materials which are non-toxic and can be sterilized. Such a heater element must also be flexible so as not to increase the stiffness of the catheter body.

In prior art heat-type thermodilution catheters, either the heater element temperature is not monitored, or the temperature is measured with a second thermometer. Use of a second thermistor significantly adds to the cost of the catheter and provides a temperature measurement, but only at a single point. Accordingly, the measured temperature might not be representative of the surface temperature as a whole. Not monitoring heat or temperature does not allow for detection of undesirable events (e.g. low flow condition).

Gibbs, in an article entitled "A Thermoelectric Blood Flow Recorder in the Form of a Needle", *Proc. Soc. Exp. Biol. & Med.*, Vol. 31, 1933, Pages 141–146, has suggested using the principle upon which a hot-wire anemometer operates to measure blood velocity. However, as noted by Gibbs in that article, such a technique has been limited to peripheral vessels and cannot give absolute blood volumetric flow rates, only velocity.

It is clear that there exists a long and unfilled need in the prior art for an improved system for maintaining the surface temperature of a thermodilution catheter heater element within safe physiological limits.

SUMMARY OF THE INVENTION

Accordingly, it is an object of the invention to provide a system for maintaining the surface temperature of a thermodilution catheter heater element within safe physiological limits.

It is further an object of the invention to provide such a system, which does not necessitate a secondary temperature measuring transducer for monitoring the surface temperature of the heater element.

It is further an object of the invention to provide a system for maintaining the surface temperature of a thermodilution catheter heater element which adjusts the supply of power to the catheter heater element in response to the core temperature of the heater element.

It is yet further an object of the invention to provide a system for maintaining the surface temperature of a thermodilution catheter heater element which is capable of testing the accuracy of its calibration prior to operation.

To achieve the above-referenced and other objects of the invention not specifically set forth, a system according to a first aspect of the invention for keeping the surface temperature of an electric resistance-type heater element in a thermodilution catheter within safe physiological limits includes a core temperature monitor for monitoring a core temperature of the electric resistance-type heater element; a power monitor for monitoring the amount of electric power that is supplied to the heater element; surface temperature calculating structure, in communication with the core temperature monitor and the power monitor, for calculating the surface temperature of the heater element; and detection structure, in communication with the surface temperature calculating structure, for determining whether a potential physiologically harmful temperature condition exists.

According to a second aspect of the invention, a system for keeping the temperature of an electric resistance-type heater element in a thermodilution catheter within safe physiological limits includes a core temperature monitor for monitoring a core temperature of the electric resistance-type heater element; a power monitor for monitoring the amount of electric power that is supplied to the heater element; a power source for supplying power to the heater element; and control structure in communication with the core temperature monitor and with the power monitor for controlling the amount of power that is supplied to the heater element by the power source, whereby the temperature of the heater element is kept within safe physiological limits.

According to a third aspect of the invention, a heater resistance verification system for verifying, in vivo, the calibration of a thermodilution catheter system of the type which utilizes an electric resistance-type heater element includes structure for measuring, in vivo, the temperature of blood which is in contact with the catheter; a power supply for supplying electric power to the heater element; a power monitor for monitoring the amount of electric power that is supplied to the heater element by the power supply; a resistance monitor for monitoring the electrical resistance of the heater element; and control structure in communication with the temperature measuring means, the power supply, the power monitor and the resistance monitor for (a) empirically determining the relationship between supplied power and heater element resistance under the in vivo conditions; (b) using the empirically determined relationship to estimate what heater element resistance would be at a reference temperature; (c) comparing the estimated heater element resistance at the reference temperature with the known heater element resistance at the reference temperature; and (d) determining whether the difference between the estimated heater element resistance and the known heater element resistance exceeds a predetermined maximum.

A method according to a fourth aspect of the invention for keeping the surface temperature of an electric resistance-type heater element in a thermodilution catheter within safe physiological limits includes the steps of: (a) monitoring a core temperature of the electric resistance-type heater element; (b) monitoring the amount of electric power that is supplied to the heater element; (c) calculating the surface temperature of the heater element, based at least in part on core temperature and power; and (d) determining, based at least in part on surface temperature, whether a potential physiologically harmful temperature condition exists.

A method according to a fifth aspect of the invention for keeping the temperature of an electric resistance-type heater element in a thermodilution catheter within safe physiological limits includes the steps of: (a) monitoring a core temperature of the electric resistance-type heater element; (b) monitoring the amount of electric power that is supplied to the heater element; and (c) controlling the amount of power that is supplied to the heater element based on the core temperature of the heater element, whereby the temperature of the heater element is kept within safe physiological limits.

A heater resistance verification method according to a sixth aspect of the invention for verifying, in vivo, the calibration of a thermodilution catheter system of the type which utilizes an electric resistance-type heater element includes the steps of: (a) empirically determining the relationship between supplied power and heater element resistance under the in vivo conditions; (b) using the empirically determined relationship to estimate what heater element resistance would be at a reference temperature; (c) comparing the estimated heater element resistance at the reference temperature with the known heater element resistance at the reference temperature; and (d) determining whether the difference between the estimated heater element resistance and the known heater element resistance exceeds a predetermined maximum.

A system for measuring the surface temperature of an electric resistance-type heater element in a thermodilution catheter according to a seventh aspect of the invention includes a core temperature monitor for monitoring a core temperature of the electric resistance-type heater element; a power monitor for monitoring the amount of electric power that is supplied to the heater element; and surface temperature calculating means, in communication with the core temperature monitor and the power monitor, for calculating the surface temperature of the heater element. These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 1 is an overall perspective view illustrating the proximal end of a catheter for measuring cardiac output in accordance with the present invention;

FIG. 2 illustrates a cross-sectional view of the catheter of FIG. 1 showing the filament lead lumen which receives the heating filament leads and/or heating element in accordance with the invention;

FIG. 5 illustrates a second embodiment of a distal end of the catheter of the invention for use in retro grade measurement, wherein the heating filament is wound about a body wall portion of the catheter and is enclosed within an outer sheath;

FIG. 6 illustrates a third embodiment of a distal end of the catheter of the invention for use in retro grade measurement, wherein a "pigtail" tip is provided to prevent blood vessel rupture;

FIG. 7 illustrates an embodiment wherein the heater element and its supporting sheath are inserted into the lumen of the catheter of FIG. 1;

DETAILED DESCRIPTION OF THE PREFERRED EMBODIMENT(S)

Figure 3:
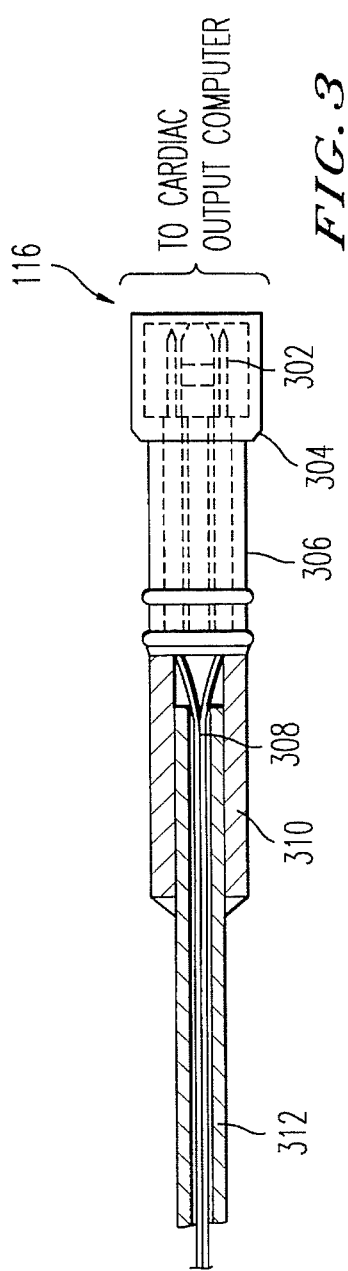
FIG. 3 illustrates a detailed view of the heater connector in the catheter of FIG. 1.

1. Description of the Embodiments Shown in FIGS. 1–8

A system in accordance with preferred exemplary embodiments of the invention will be described below in detail with reference to FIGS. 1–8. It will be appreciated by those of ordinary skill in the art that the description given herein with respect to those embodiments is for exemplary purposes only and is not intended in any way to limit the scope of the invention. All questions regarding the scope of the invention may be resolved by referring to the appended claims.

A detailed description of intra vascular catheters is not given herein, for the features of different types of catheters, namely flow-directed pulmonary artery catheters, left ventricular angiography catheters, and the like are well known to those familiar to the art. Some unique features of such catheters are described by way of example in U.S. Pat. Nos. 3,746,003; 3,634,924; 3,995,623; 4,696,304; 4,718,423; and 4,721,115.

FIG. 1 illustrates a proximal end of a catheter arrangement 10 in accordance with a first embodiment of the invention. As shown, the catheter arrangement 10 comprises a flexible catheter body portion 100 which is adapted for insertion into a blood vessel of a patient and is formed of a non-toxic material such as polyvinyl chloride (PVC). The catheter body portion 100 is also preferably coated with heparin to prevent blood clot formation. At a distal tip of the catheter body portion 100, an inflatable balloon 102 is provided for a flow-directed measurement so that the catheter arrangement 10 may be inserted into the right ventricle of the heart using the customary flow-directed insertion technique. Within a couple of centimeters of the balloon 102 is disposed a temperature sensing device such as a thermistor or thermocouple 104 for measuring the temperature of the flowing blood. This measurement is then used in the thermodilution volumetric blood flow calculation in accordance with known techniques, such as those described in copending patent application Ser. No. 07/510,897 to McKown et al. As shown in FIG. 1, the catheter body portion 100 for insertion into the blood vessel preferably has a length of, for example, 112 centimeters so that it is long enough to be "floated" into the right ventricle of the patient's heart using the flow-directed insertion technique. Insertion may thus be accomplished at bedside without the requirement of fluoroscopy.

At a proximal end of the catheter body portion 100 is provided a catheter body junction 106 through which devices such as a PA distal lumen hub 108, a proximal injectate lumen hub 110, a thermistor or thermocouple connector 112, a balloon inflation valve or stopcock 114, and a heater connector 116 may be inserted into respective filament lead lumens of the catheter body portion 100. In particular, as shown in FIG. 2, the catheter body portion 100 of the invention may comprise an outer layer 202 and an intermediate layer 204 which adheres the outer layer 202 to body wall portion 206 of catheter body portion 100. As shown, body wall portion 206 separates the internal area of catheter body portion 100 into one or more lumens for accepting the peripheral devices 108–116. As will be appreciated by those skilled in the art from the following description, one of the lumens permits leads from heater connector 116 to communicate with a downstream heating filament disposed within or about the catheter body portion 100. Although multiple lumens are shown, there is no reason that different leads cannot share a common lumen.

In accordance with the invention, the heater connector 116 communicates with a cardiac output computer so as to receive power signals for controlling the heating filament. Connector 112 forwards temperature changes measured by the thermistor or thermocouple 104 back to the cardiac output computer for calculation of the cardiac output in accordance with a known thermodilution technique. A presently preferred thermodilution technique is that described in copending patent application Ser. No. 07/510,897, to McKown et al. and assigned to the present Assignee. That patent application discloses a cardiac output computer which utilizes an improved stochastic technique from that disclosed by Yelderman in U.S. Pat. No. 4,507,974, for applying heat to the blood stream and evaluating the results in accordance with a cross-correlation of the input with the measured output. The disclosure of that application is hereby incorporated by reference as if set forth entirely herein.

The heater connector 116 is shown in more detail in FIG. 3. As shown, heater connector 116 comprises electrical connector 302 within a plug portion 304 for electrically communicating with the cardiac output computer. The electrical connector 302 communicates through electrical connections in casing 306 with heater wire leads 308. Heater wire leads 308 transverse the length of the support casing 310 and the supporting sheath or heater wire lumen 312 so as to electrically communicate with the heater filament as will be described below. The supporting sheath 312 is preferably made of teflon so as to be flexible yet strong. In accordance with the invention, the supporting sheath 312 supporting the heater wire leads 308 is inserted into a lumen of the catheter body portion 100 to facilitate electrical connection to the heating element. Electrical leads may be similarly "fished" through a lumen to connect to thermistor or thermocouple 104. A more complex connector will be described below with respect to FIG. 8.

Figure 4A:
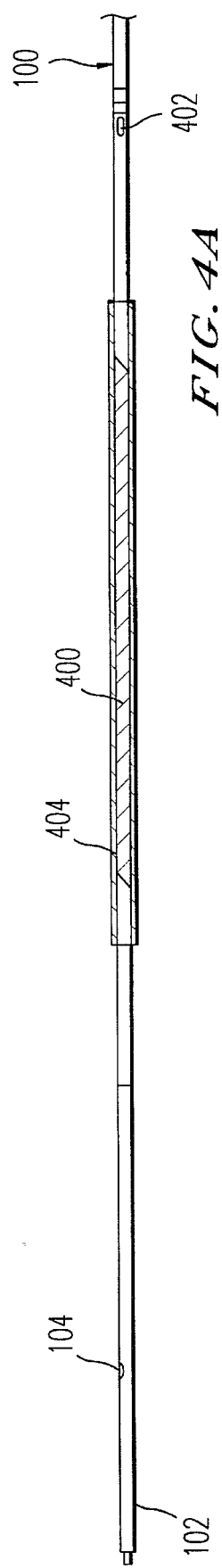
FIG. 4(a) illustrates a first embodiment of a distal end of the catheter of the invention for use in flow-directed measurement wherein the heating filament is wound about a body wall portion of the catheter and is enclosed within an outer sheath.

FIG. 4(a) illustrates the manner in which the heating filament 400 is wrapped about the outer layer 202 of the catheter body portion 100 in accordance with a first embodiment. As shown, the heating filament 400 is formed so as to be very thin and flat so that it can be wrapped in a non-overlapping manner about the outer layer 202. As shown, an injectate or pacing port 402 may also be provided proximal to heating filament 400. The heating filament 400 is preferably wrapped to extend approximately 5 to 10 centimeters along the outer layer 202 and is disposed so as to be approximately 14 centimeters from the distal tip having balloon 102 of the catheter body portion 100. The heating filament 400 is then surrounded by a thin outer sheath 404 to prevent the heating filament 400 from directly contacting the patient's blood.

Generally, the heating filament 400 is printed on a substrate as a sandwich. The substrate of the heating filament consists of a thin material that is capable of being incorporated into a filament material which is preferably flexible and has the ability to bond with an adhesive. It must also have good heat transfer properties which allow for the conduction of the filament generated heat to the exterior of the outer sheath 404 so as to be applied to the blood. An additional layer of material with high thermal conductivity (e.g., metal foil) may be added to the heater sandwich to help create a more uniform surface temperature. The filament materials of the invention include, but are not limited to, Mylar and Kapton. On the other hand, the filament material, which is adhered to the substrate, can be any material which has a high temperature coefficient of resistance, i.e. greater than 0.001 $\Omega/\Omega-°C.$, and low thermal capacitance and high thermal conductivity. The material must be capable of being incorporated into the filament substrate and must be capable of being fabricated in thin layers so as to form a sandwich (e.g. Kapton—adhesive—filament metal—adhesive—Kapton). Alloys for the filament material include, but are not limited to, an alloy of 70% nickel and 30% iron or an alloy of 29% nickel, 17% cobalt and 54% iron.

An adhesive material must be selected which is capable of binding to both the outer sheath 404 and the catheter body portion 100, and to the filament substrate, or in some applications, directly to the filament material. The adhesive must be capable of being applied in a thin, even layer, must be non-toxic, must not weaken with time, must tolerate heat from the filament, must tolerate continual flexing, and must bind well in a wet environment (i.e., blood). Such adhesives include, but are not limited to, pressure sensitive adhesives such as Densil.

In another embodiment, the adhesive, the outer sheath material and the electrical resistive components may all be incorporated into one material. The electrical leads are then connected to the material, which is formed as a sheath or wrapping material and applied directly to the outer layer 202 of the catheter body portion 100 or incorporated during the manufacturing process directly into the outer layer 202 of the catheter body portion 100.

In accordance with the invention, the thin heating filament materials of the invention may be spirally wound around the catheter body portion 100 to form a heating filament 400 as just described. Although the filament substrate or filament heater material may be exposed directly to the blood environment as in the prior art devices, in accordance with the invention the filament substrate and/or filament material are preferably enclosed, surrounded by, or incorporated within an outer sheath 404 for assuring that fragments of filament or filament substrate do not become dislodged into the blood environment. Moreover, by providing a covering material or outer sheath 404, the exterior of the catheter may be made smoother and hence more comfortable for the patient during insertion into the blood vessel. Of course, this structure is made possible because the above-mentioned heater filament material may be formed into a very thin filament which may be non-overlappingly wound about the catheter body portion 100. However, the sheath 404 must also be very thin and flexible and is preferably an adhesive applied by any of a number of techniques over the filament or filament substrate. Such adhesives include, but are not limited to, Master Bond EP37. The resulting catheters are then preferably coated with heparin to prevent blood clot formation.

Figure 4B:
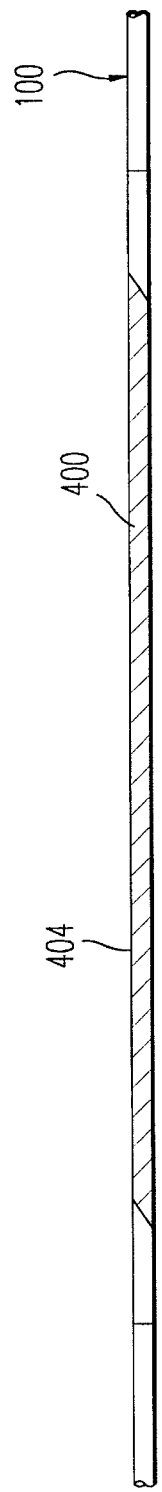
FIG. 4(b) illustrates a modification of the first embodiment wherein the heating filament is flush with the adjacent section of the catheter body so as to prevent an increase in the catheter cross-section.

Regardless of the type of filament material used or the number of layers of materials or sandwich composition, the catheter body may be reduced in diameter in the region where the filament sandwich is wound, as shown in FIG. 4(b). The reduction in catheter body diameter is made such that, when the filament sandwich is added, the resulting total diameter in the region of the heating filament is equivalent to the diameter of the adjacent catheter body portion without the filament material. This achieves a uniform transition to the region of the catheter filament, thereby eliminating problems associated with insertion, removal and thrombus formation in regions of irregularities.

In accordance with the invention, a particularly attractive method for applying the sheath 404 is to use a flexible sheath material which can be applied over the filament, filament substrate, and filament-to-catheter body adhesive. Preferably, a material is used which has an appropriate modulus of elasticity and elongation. The material may be fabricated by a technique such as extrusion so that its resting lumen diameter is less than that of the catheter filament sub-assembly. The sheath material or "tube" may then be expanded using a "vacuum expander" to a size larger than the catheter and attached filament sub-assembly. The catheter and sub-assembly may then be passed into the vacuum expander containing the expanded sheath, positioned in place, and then the vacuum released. The sheath then shrinks, reduces or collapses around the filament sub-assembly so as to maintain a certain tension with the underlying components. Preferably, the vacuum expander contains a chamber which allows for the placement of the sheath material so that the ends of the sheath material may be secured to form a closed chamber between the outer wall and ends of the sheath material and the surrounding chamber. The chamber dimensions may be such as to allow for the expansion of the sheath to a size which is large enough to accept the passage of the catheter body portion 100 and the attached filament sub-assembly. The sheath then may be expanded by applying a vacuum to the chamber and/or positive air pressure to the inside of the sheath. Expansion of the sheath may also be improved by applying heat to the expansion chamber. Conversely, a blow molding technique may be used in accordance with known techniques. A material which may be manufactured to have such a thin wall, an appropriate modules of elasticity, and an appropriate elongation includes, but is not limited to, Tecoflex™.

Another method of sheath application in accordance with the invention utilizes shrink material. The sheath may thus be fabricated to be slightly larger than the catheter body portion 100 and the attached filament sub-assembly. It is then applied without the vacuum expander, and when the sheath material is situated in the proper location, it is reduced in size by the application of heat. Again, the proper wall thickness and beginning dimensions are chosen such that, following the reduction in size, appropriate tension is maintained with respect to the underneath filament sub-assembly.

Preferably, as described above, the cylindrical heating filament 400 is approximately 10 centimeters in length and is wrapped about the outer wall 202 of the catheter body portion 100 beginning distally about 15 centimeters from the distal tip of the catheter. Then, when the catheter is positioned with the distal tip in the pulmonary artery during a flow-directed measurement, a proximal fluid infusion port of the catheter will lie in the right atrium of the heart or superior vena cava while the distal fluid infusion port will lie in the right ventricle.

An alternative embodiment of the invention for measuring blood flow in a "retro grade" fashion, such as in the hepatic vein, is shown in FIG. 5. As shown, the heating filament 500 and the thermistor or thermocouple 502 are in reversed positions on the catheter body portion 100 because of the reversed blood flow direction. Since this type of catheter is inserted into the blood vessel against the blood flow, insertion generally requires the use of fluoroscopy for directing the catheter into place for measurement. Since the embodiment of FIG. 5 is not a flow-directed catheter, a balloon at the distal tip is not used.

The alternative embodiment of FIG. 6 may also be used for measuring blood flow in a "retro grade" fashion, as in the left ventricle of the heart, whereby the heating filament 600 and thermistor or thermocouple 602 are in reversed positions on the catheter body portion 100 as in the embodiment of FIG. 5. As in the FIG. 5 embodiment, insertion generally requires fluoroscopy and a balloon tip is not used. However, a pigtail tip 604 is preferably used in this embodiment to prevent vessel rupture.

During operation, since the heating filament formed as described above is used primarily to insert heat into the blood stream, it will rise to a temperature higher than the surrounding environment. Thus, it is necessary to know the filament temperature since, should the temperature become excessive, damage could result to the surrounding blood and tissues. Normally, a second temperature sensing device such as a thermistor or thermocouple would need to be embedded next to the filament to measure its temperature. However, by using a filament material which has a high temperature coefficient of resistance as herein described, not only can it be used as a heat supplier, but it can also serve as its own temperature sensing device. For example, resistance of any material is measured as follows:

$$R = \frac{\rho \cdot l}{A},$$

where

ρ is the resistivity, l is the length, and

A is the cross-sectional area.

Then:

$$\Delta R = \frac{\Delta \rho \cdot l}{A},$$

and if α, the mean temperature coefficient of resistivity, is defined as:

$$\alpha = \frac{1}{\rho} \cdot \frac{\Delta \rho}{\Delta T},$$

where

Δρ is the change in the coefficient and

ΔT is the change in temperature, then:

$$\Delta T = \Delta R \frac{A}{l \cdot \alpha \cdot \rho}.$$

Then, by measuring the current (i) and the voltage (v), both delivered power and resistance of the filament can be simultaneously measured as:

$$\frac{\Delta v}{\Delta i} = \Delta R.$$

The heating filament 400 of the invention typically consists of a cylindrical design which is approximately 5–10 centimeters in length. Heater wire leads 308 are attached to the heating filament 400, and the heating filament 400 is placed at the desired distance from the thermistor or thermocouple 104 (10 cm in FIGS. 4(a) and (b)). Then, as previously described, the heat transfer is such that the heat passes from the heater filament 400 through the outer sheath 404 into the blood. Of course, the heating filament 400 must be flexible such that it does not increase the stiffness of the catheter body portion 100.

In accordance with another embodiment of the invention, as shown in FIG. 7, the heating filament 400 may be made as a mobile module supported by a flexible supporting member 700 which can be inserted or withdrawn from the catheter lumen after the catheter has been inserted into the patient. This has the advantage that the catheter can be inserted into the patient when it is not known whether measurement of blood flow is required. Should the measurement of blood flow become desirable, the mobile filament module can be inserted and the measurement started. This feature of the invention is particularly helpful in a clinical setting, for although pulmonary artery catheters were originally designed to measure distal pressure, more features have been added such as bolus thermodilution cardiac output measurements, cardiac pacing and mixed venous saturation. Thus, the clinical problem now is to know which catheter to use, for not all patients require all measurement modalities.

The invention is thus designed as a pulmonary artery catheter which has one or more ports and/or lumens which will accept the particular modules (as shown in FIG. 1) for a particular measurement modality. For example, for a 4-lumen catheter of the type shown in cross-section of FIG. 2, one lumen may be dedicated to measuring distal catheter pressure, one lumen may be dedicated for distal balloon inflation and passage of two distal thermistor or thermocouple leads, one lumen may be dedicated to proximal fluid infusion, and the fourth lumen may be left open. Moreover, another lumen may receive a module for measuring mixed venous oxygen saturation including a fiber optic bundle. Other modules may be designed at the user's discretion.

During use, the pulmonary artery catheter of the invention (with the vacant lumen) is inserted in the usual and customary fashion. After insertion, if so desired, the physician or the user may electrically pace the heart by passing a modules or wire through the vacant catheter lumen so as to connect the proximal end of the wire to the appropriate electronics. Such a concept of a removable pacing wire has been previously described by Swendson, et al. in U.S. Pat. No. 4,759,378, for example. On the other hand, if the measurement of mixed venous saturation is desired, the pacing wire modules would be removed and a fiber optics modules inserted in the vacant lumen for measuring mixed venous saturation, and the proximal end of the fiber optics would be attached to the appropriate electronics. Such fiber optics techniques for measuring mixed venous saturation are described by Willis, et al. in U.S. Pat. No. 4,718,423, for example. However, the fiber optics technique taught by Willis, et al. is not removable; therefore, if cardiac output is desired, the vacant lumen must be replaced with the thermal transducer filament or other apparatus modules for performing cardiac output measurement. Of course, the scope of the invention is not limited to just these modalities, but includes any modalities which could be used at the user's discretion.

Thus, in accordance with the invention, the heating filament 400 is placed either around the catheter body portion 100 but within an outer sheath 404 or is placed within the catheter body portion 100, namely, in a lumen thereof. In either case, the heating filament 400 does not directly contact the patient's blood. This is in marked contrast to previous embodiments wherein the heating elements are generally placed on the exterior of the catheter or the filaments are used as unattached free-floating pieces. Instead, in accordance with the present invention the heating filament 400 is placed such that the heat transfer properties of the catheter body portion 100, the outer sheath material and heating filament material allow the transmission of heat to the exterior environment, namely, the blood stream. Such an arrangement has significant implications since an internally placed heating filament reduces the probability of harmful blood clot formation, electrical leakage currents, or unusually high filament blood contact temperatures.

When a thermodilution catheter in accordance with the invention is connected to a cardiac output computer via heater connector 116, an electrical current is applied to the heating filament in the form of pulses. When the heating filament is activated, an approximate average of 7.5 watts of power may be delivered to the heating filament. During operation, as described above, the cardiac output computer may continuously measure and monitor the filament temperature so as to limit the estimated surface temperature to a maximum of 45° C. (which corresponds to an average surface temperature of about 41.5° C., depending upon the material composition and thickness). For example, in the event the heating filament core temperature exceeds a power dependent threshold, for more than, say, 15 seconds at full power, the delivered heating filament power is reduced. If the estimated heating filament surface temperature exceeds 45° C. for more than, say, 4° C.—seconds at any power, the heating filament power may be shut off and a panel alarm activated. In practice, this prevents the peak surface temperature from exceeding 45° C. Moreover, the average catheter surface temperature should not exceed 41°–5° C., since the power will be switched "ON" approximately 50% of the time. Furthermore, if the average cardiac output exceeds 3.5 liters/minute, the catheter's average surface temperature will generally remain below 39.5° C. Thus, regulation of power to the catheter only becomes an issue when the cardiac output becomes less than about 3.5 liters/minute. However, since the power to the heating filament is reduced or shut off as the estimated filament surface temperature reaches 45° C., the heating element of the invention can be made relatively fail-safe through closed-loop control of the surface temperature.

By using a power source which is a constant voltage source, an increasing catheter filament temperature can be directly detected as an increasing filament resistance which reduces the power delivered to the heating filament. In this manner, the actual current and voltage to the catheter filament may be continuously monitored. From the values of current and voltage, a delivered power may be calculated which is needed to calculate flow, and the filament resistance may be calculated and used for computing the filament core temperature. Thus, at all times, the actual filament core temperature is known. Preferably, the following algorithm is followed to insure that the filament temperature remains within safe limits:

(1) When the cardiac output computer starts, the delivered power to the heating filament is maintained at approximately 4 watts average power.

(2) The filament core temperature is monitored for several seconds.

(3) If the peak filament core temperature has not exceeded 49° C., the filament power is increased to an average power of 7.5 watts.

(4) If at any time the peak filament core temperature exceeds 56° C., the delivered filament power is reduced.

(5) If at any time the estimated filament surface temperature exceeds 45° C. for more than, say, 4 degree-seconds, the computer shuts off and displays an error message.

The cardiac output may be measured continuously by turning the heating filament on and off in a predetermined pattern and generating a characteristic thermodilution curve by a mathematical process such as cross-correlation as described in the afore-mentioned co-pending application, U.S. Ser. No. 07/510,897 to McKown et al. A detailed discussion of bolus thermodilution and pulse thermodilution techniques are described in that application.

By using an indicator dilution method in accordance With a stochastic system of the type described in the afore-mentioned related application, Ser. No. 07/510,897 to McKown et al., cardiac output may be measured in a noisy environment even when a small heat input source as herein described is used. The stochastic techniques of the type described in the afore-mentioned application are different from classical empirical techniques in that the input signal or energy is applied over a period of time, and the nature of the statistical properties of the input and output signals are of interest. Thus, during operation in accordance with this technique, the supplied heat in accordance with the present invention will produce a small temperature change in the flowing blood which is detected at the distal thermistor or thermocouple 104. Through a mathematical procedure known as cross-correlation, a scaled characteristic thermodilution "wash-out" curve is reconstructed. The cardiac output may then be calculated by measuring the area under this "wash-out" curve if the amount of heat delivered to the blood by the heating filament is also known. An indicator thermodilution equation for calculating flow is described in the afore-mentioned application.

In the calculation of cardiac output using such thermodilution techniques, it is necessary to know certain properties about the measuring transducer, such as the thermistor or thermocouple 104, and the heat application or heating filament efficiency, for in the manufacturing process it is difficult to produce either thermistors or thermocouples 104 or heating filaments 400 which uniformly have the same properties. Thus, to reduce the errors which would be introduced into the calculation of cardiac output due to these variances, it is necessary to calibrate or measure the physical properties of both the thermistor or thermocouple 104 and the heating filament 400. Since in a clinical environment each cardiac output computer may be attached over time to various pulmonary artery catheters and to eliminate the need for the user to manually transcribe these calibration numbers to the computer, a coding technique has been developed in accordance with the invention to pass the calibration information.

Prior art thermodilution catheters and pulse oximeter sensors have used resistors to code the values for thermistors or LEDs. For example, New et al. in U.S. Pat. No. 4,700,708 use a resistor to calibrate LED wavelengths on a pulse oximeter. However, the present inventors know of no previous attempt to code the filament calibration for transferring the calibration information of the heating filament solely or the calibration information of the heating filament and thermistor or thermocouple together. Thus, in accordance with the present invention, calibration of the heating element may be conducted by measuring the heater resistance at a known temperature. The catheter assembly can then use the previously calibrated thermistor or thermocouple and a built-in ohm meter to establish a calibrated reference point for the heater element. This approach has the advantage of calibrating the heater immediately prior to use in a patient at the patient's body temperature. Such an accurate calibration of heater resistance and temperature is necessary to accurately monitor heater temperature to insure patient safety.

The calibration circuit may include passive electronic components such as resistors, inductors and capacitors such that the value of the components correspond to a particular calibration value or number according to a predetermined table. On the other hand, active electronic components including numerous nonlinear components may be used such that a particular performance corresponds to a particular calibration number or value. Such calibration information is preferably stored in a memory component such as a ROM (Read Only Memory), a RAM (Random Access Memory), a nonvolatile memory device, or another type of memory or digital device. The calibration information preferably includes codes that represent the filament resistance, filament efficiency, and other parameters. If properly selected, one or more electronic components may be used to encode the calibration information of the thermistor or thermocouple, such as its $\beta$ value, and the filament resistance, filament efficiency and other parameters.

Thus, the calibration information for both the thermistor or thermocouple 104 and the heating filament 400 may be encoded by one or more active or passive electronic components or these values may be stored in a suitable memory device. The cardiac output computer may then decode this information and incorporate it into the calculation of cardiac output. However, this step may be eliminated if the actual appropriate software is contained in the catheter itself. For example, a memory device such as a ROM may be contained in the catheter with a portion of the software utilized by the cardiac output computer resident within it. Such information might include program segments or historical patient data. Thus, when the catheter is connected to the cardiac output computer, prior to the beginning of processing for determining the cardiac output, the software or program segment contained in the catheter memory device (ROM) may be transferred to the main software program of the cardiac output computer. This feature of the invention also provides an additional safety feature, for the cardiac output computer will not start until it has transferred the program segment and incorporated this segment into its own program.

Figure 8:
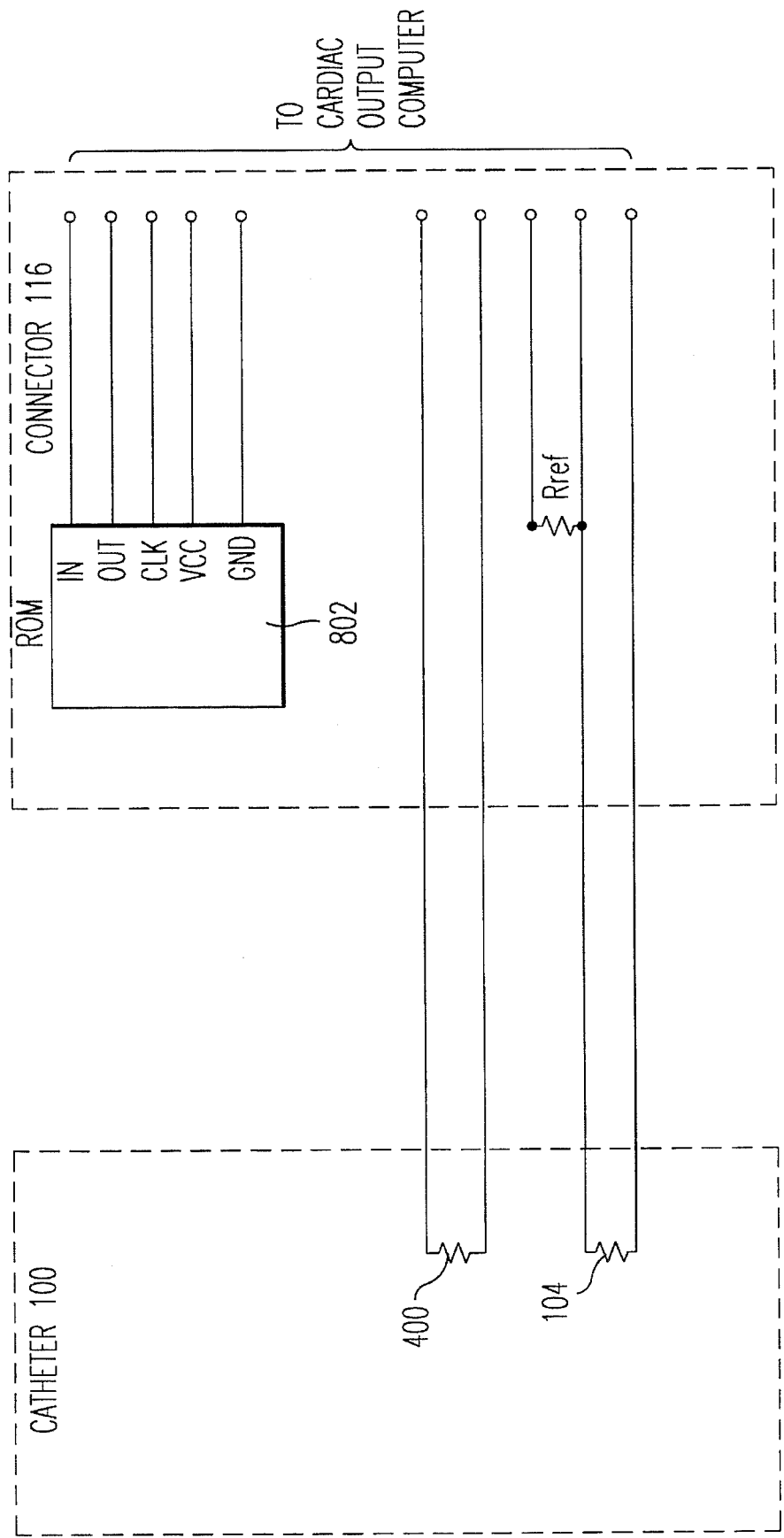
FIG. 8 illustrates a calibration circuit having a ROM in accordance with a preferred embodiment of the invention.

The calibration circuitry of the type just described can be seen by way of example in FIG. 8. As should be apparent to one of ordinary skill in the art, the calibration circuit of FIG. 8 is quite different from that used in typical prior art thermodilution catheters. In particular, classic thermodilution catheters use calibration resistances which are connected in series with the thermistor or thermocouple. In such devices, the reference resistor is calibrated to match the thermistor or thermocouple for a standard temperature. In this manner, compensation for variability in the thermistors or thermocouples may be achieved. However, by using the calibration circuit of the invention wherein a ROM containing calibration data is included within the connector of the catheter, such a reference resistor for calibration purposes is not needed. Such a ROM is shown as ROM 802 of connector 116 in FIG. 8.

Preferably, the software module referred to above is stored in the ROM 802 and includes such things as the format version for the calibration data, trademark information, historical patient data (such as cardiac output for the previous several hours) or whatever information is desired for controlling the cardiac output program. Thus, by placing the encoded calibration data within the ROM 802 and placing the ROM 802 on the catheter, the thermistor or thermocouple reference resistance may be eliminated. In addition, only a catheter having a ROM 802 storing the necessary information for operating the program of the cardiac output computer may be used in conjunction with the cardiac output computer to obtain the desired calculation.

Although a number of exemplary embodiments of the invention have been described in detail above, those skilled in the art will readily appreciate that many additional modifications are possible in the exemplary embodiments without materially departing from the novel teachings and advantages of this invention. For example, rather than wrapping the heating element 400 around the catheter body portion 100, the heating element may be included in the body wall portion 202 of the catheter body portion 100. In addition, the heating element 400 may be made in multiple contiguous sections, whereby by measuring the temperature of each section it is possible to determine whether one section is malfunctioning. Such malfunctions could be due to filament abnormalities or due to physiologic aberrations such as clotting. The discrepancy in temperature would alert the user to a potential problem. However, such a section arrangement would require additional electrical leads, and the catheter would need to be modified accordingly. Alternatively, the heating filament of the invention may be used in conjunction with a guide wire for angioplasty, where the thermistor or thermocouple will be miniaturized and placed on the guide wire, and the heater placed upstream on the guide wire. The resulting device may then be inserted into a catheter lumen of the type described herein. In addition, the heating filament may be placed ahead of or behind balloon 102 as desired.

Accordingly, all such modifications are intended to be included within the scope of this invention as defined in the following claims.

DESCRIPTION OF THE EMBODIMENT OF FIGS. 9–17

Figure 15A:
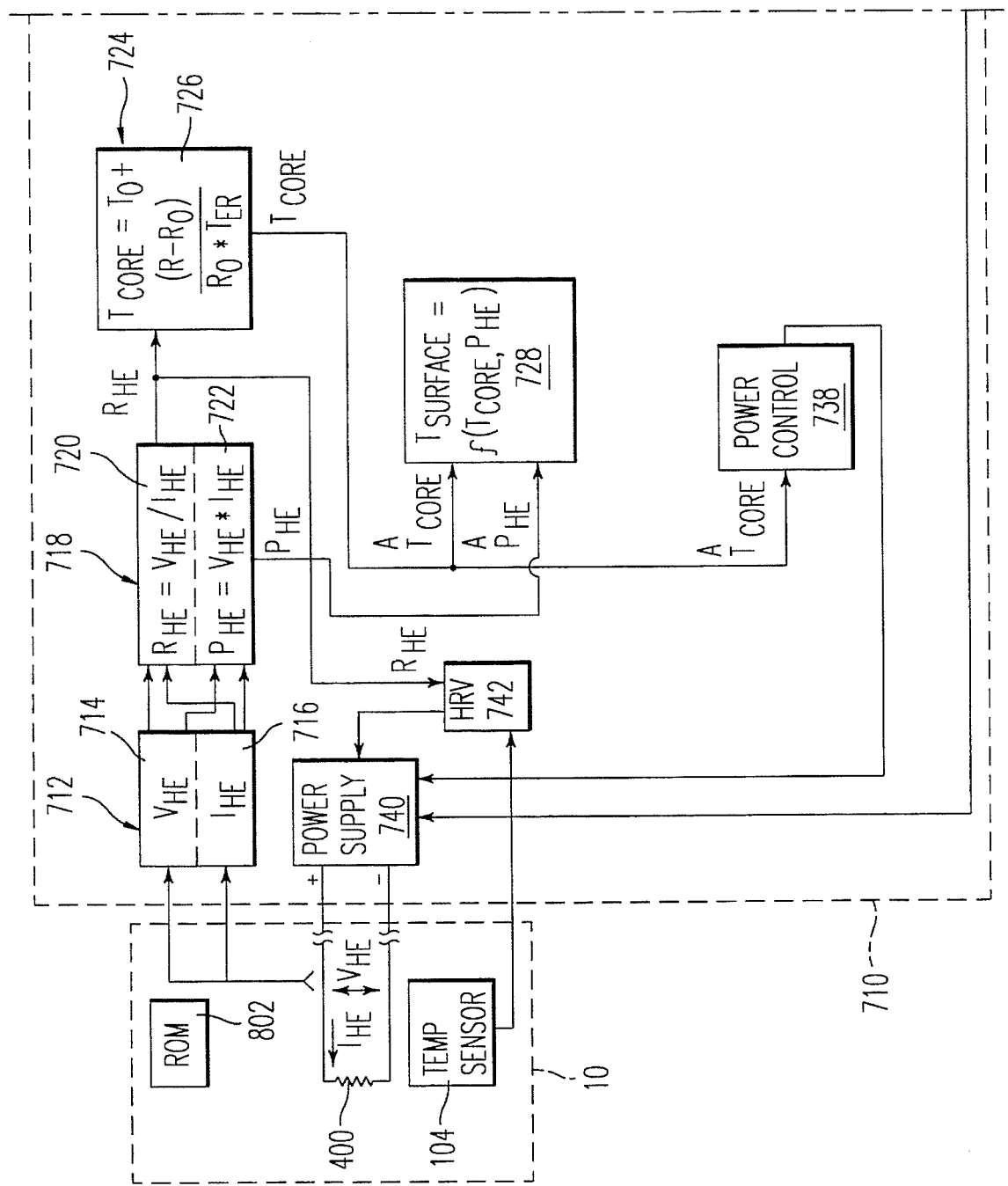
FIGS. 15(a) and 15(b) are a schematic flow diagram depicting the power control and safety shut-off systems and methods according to a preferred embodiment of the invention.
Figure 15B:
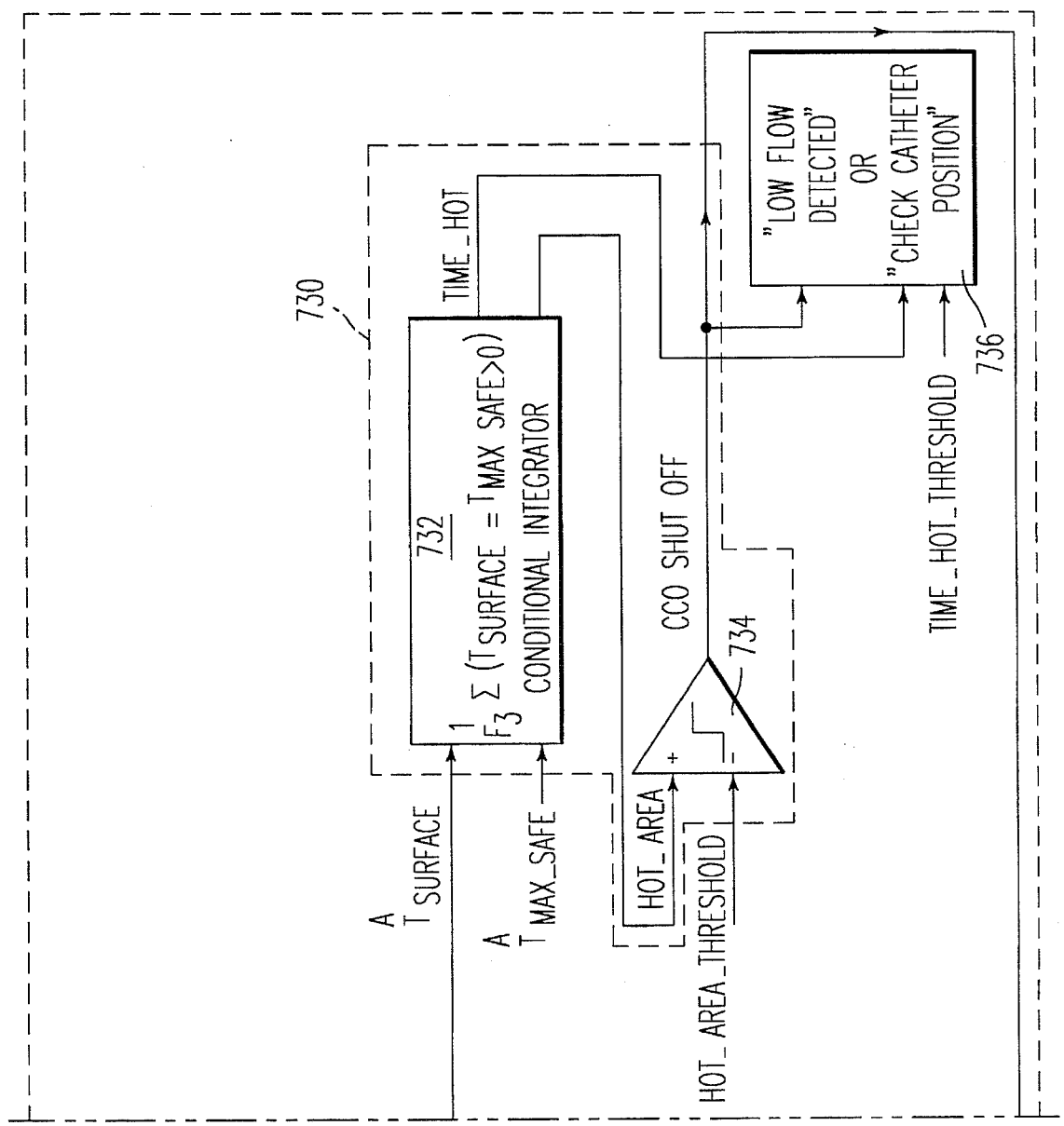

Referring to FIG. 15, it will be seen that the cardiac output computer ("COC") 710 is connected to catheter arrangement 10 such that it is in communication with the heating element 400, the thermistor or thermocouple 104 and the ROM 802. The ROM 802 and the technical details associated therewith are fully disclosed in U.S. patent application 07/769,536 to inventors Yelderman and Quinn entitled "A Diagnostic Catheter with Memory." The disclosure in that application is hereby incorporated into this document as if set forth fully herein. Referring again to FIG. 15, it will also be seen that COC 710 includes a system which is constructed and arranged to maintain the surface temperature of heating element 400 at a level which is physiologically safe. More specifically, COC 710 is constructed and enabled to perform a safety shut-off method which provides for the automatic shut-off of power to the heater element 400 under conditions of very low measured flow, or whenever the unit is inadvertently operated with the catheter in air. COC 710 is also constructed and enabled to prevent the peak surface temperature of heating element 400 from exceeding a maximum safe temperature (in the preferred embodiment 45° Centigrade) during conditions of low flow, which in the preferred embodiment is 0.5 to 2.5 lpm. COC 710 is further constructed and enabled to perform a heater element resistance verification test which provides an in vivo system readiness test that checks the calibration of both the COC and the catheter to ensure proper operation of the safety shut-off system.

1. The Core Temperature Monitor

As will be seen in the description provided below, both the safety shut-off system and the two state power control system require the monitoring of a core temperature within heating element 400. According to one advantageous feature of the invention, the core temperature monitoring is conducted without a separate temperature measuring device. As will be discussed below, this is done by continuously measuring the voltage and current supplied to heating element 400 to calculate both the delivered power and the resistance. The core temperature is then calculated by the COC 710 based on the resistance of heating element 400, the temperature coefficient of electrical resistance ("TCR") of the metal used in heating element 400, and the known resistance of the heating element 400 at a reference temperature. In the preferred embodiment, the reference temperature and reference resistance are precalibrated into ROM 802 during the manufacturing process.

Referring briefly to FIG. 15, it will be seen that the COC 710 includes a voltage and current measuring unit 712 having a voltage measuring subunit 714 and a current measuring subunit 716. COC 710 further includes a resistance and power monitoring unit 718 which includes a resistance monitoring subunit 720 and a power monitoring subunit 722. Resistance monitoring subunit 720 receives a voltage measurement from voltage measuring subunit 714 and a current measurement from current measuring subunit 716. Similarly, power monitoring subunit 722 receives a voltage measurement from voltage measuring subunit 714 and a current measurement from current measuring subunit 716. The resistance of the heating element 400 is calculated in resistance monitoring subunit 720 by dividing voltage by current, according to Ohm's Law. This resistance value is supplied to a core temperature monitoring unit 724, also in COC 710. Core temperature monitoring unit 724 includes core temperature calculating means 726 which calculates the core temperature of heating element 400 according to the formula set forth below in Equation 1.

$$T_{core} = T_0 + (R - R_0)/(R_0 * TCR);$$  (Equation 1)

The specific numeric values for $R_0$, $T_0$ and TCR are unique to each thermodilution catheter, and they are established and stored during the manufacturing process in the catheter ROM 802.

Referring again to FIG. 15, COC 710 further includes a surface temperature calculating unit 728 for calculating the surface temperature of heating element 400. As may be seen in FIG. 15, surface temperature calculating unit 728 receives input from power monitor subunit 722, which calculates the power supplied to heating element 400 by multiplying voltage and current. Surface temperature calculating unit 728 further receives the core temperature of heating element 400 from the core temperature monitoring unit 724. Surface temperature calculating unit 728 calculates the surface temperature of heating element 400 according to the following formula:

$$T_{surface} = m_{core} * T_{core} + m_{power} * P_{element} + b;$$  (Equation 2)

Where $T_{core}$ is the core temperature estimate obtained from core temperature monitoring of unit 724; $P_{element}$ is the power applied to heater element 400, obtained from power monitoring subunit 722; $m_{core}$ is a constant relating core temperature to surface temperature under anticipated clinical conditions; $m_{power}$ is a constant relating the power delivered to the heater element to the incremental increase in surface temperature that will be created by the power under anticipated clinical conditions; and b is a numeral constant.

The specific numeric values for $m_{core}$, $m_{power}$ and b are unique to each thermodilution catheter model, and they are established and stored during the manufacturing process in ROM 802. The preferred methodology for establishing such values for a particular thermodilution catheter system will be described below with reference to example I.

EXAMPLE 1

By carefully mounting a three millimeter (0.003 inch) diameter thermocouple (Omega Engineering, type T) to the surface of the heater element 400, simultaneous core and surface temperatures can be measured at different flows and heater powers. These data allow the development of an empirical model for the surface temperature given the electrically measured heater power and core temperature.

Figure 9:
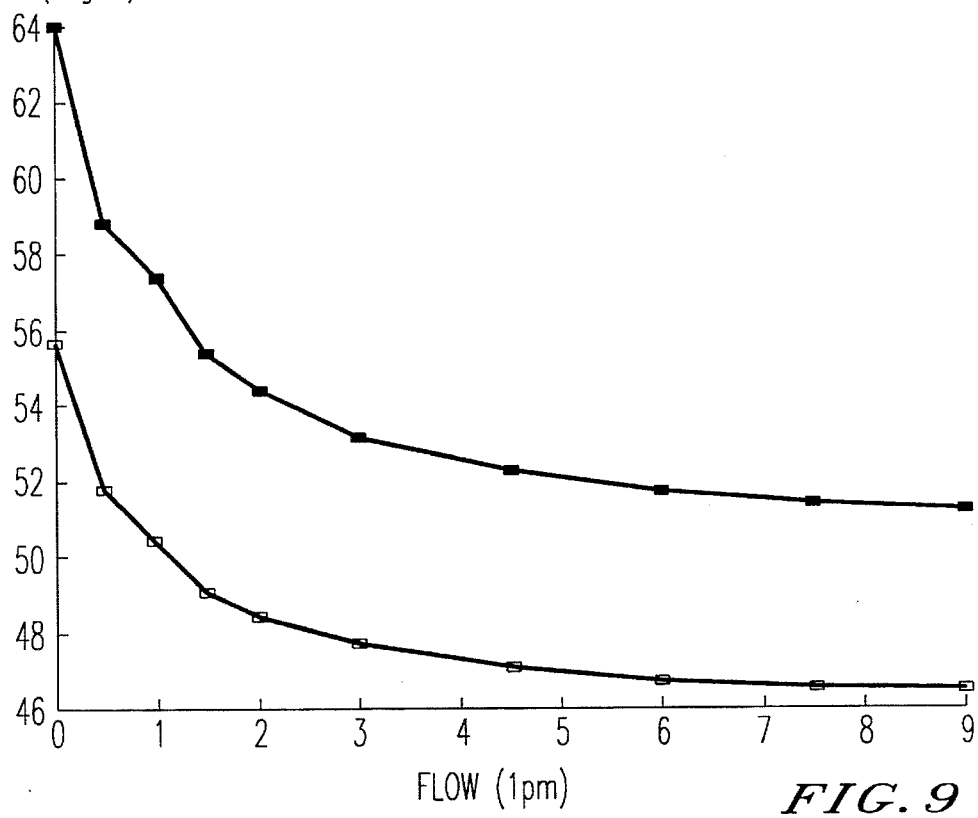
FIG. 9 is a graphical depiction of core temperature versus flow for a particular thermodilution catheter heater element in turbulent flow test conditions.
Figure 10:
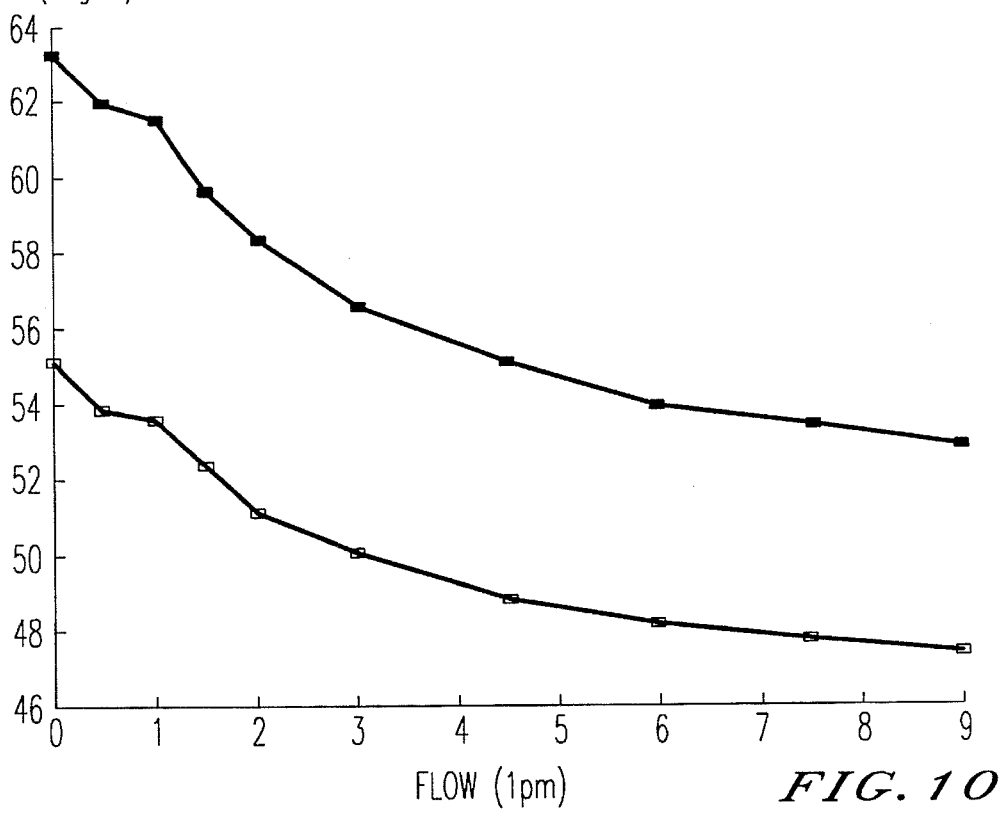
FIG. 10 is a graphical depiction of core temperature versus flow for the same catheter element depicted in FIG. 9 under laminar flow test conditions.
Figure 11:
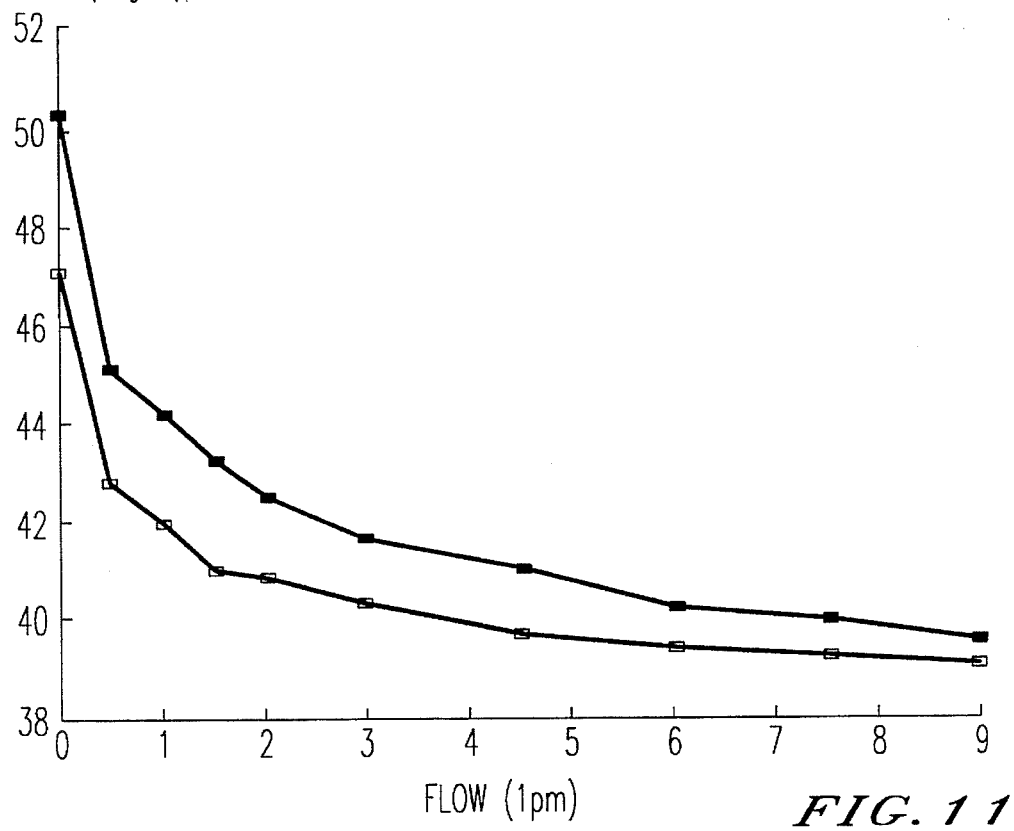
FIG. 11 is a graphical depiction of surface temperature versus flow for the catheter heater element depicted in FIGS. 9 and 10 under turbulent flow test conditions.
Figure 12:
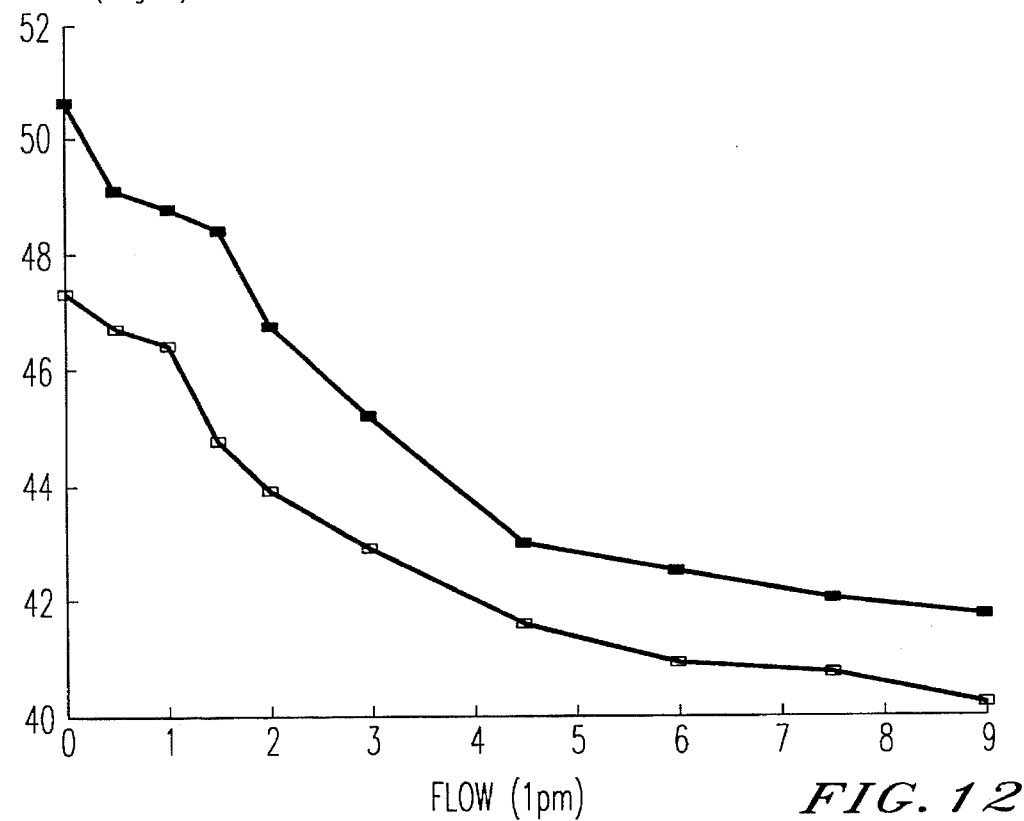
FIG. 12 is a graphical depiction of surface temperature versus flow for the catheter heater element depicted in FIGS. 9–11 under laminar flow test conditions.

FIGS. 11 and 12 show the surface temperature data that accompany the core temperature data of FIGS. 9 and 10, the turbulent and laminar flow cases, respectively. To average the effects of convection currents at zero flow, the thermocouple was positioned on the side of the horizontal catheter. These surface temperature data were obtained by visually averaging a one sample per second digital temperature display over a 15 second period.

These data were acquired using a dc power supply to continuously provide power to the heater element. A system according to the preferred embodiment of the invention, on the other hand, powers the heater with a signal derived from a pseudo random binary sequence ("PRBS") of period length 15. Since the PRBS length 15 signal is activated only $8/15$ of the time, an average surface temperature can be defined as:

$$T_{surface/ave} = (8/15) * T_{surface/on} + (7/15) * T_{bath};$$

Where $T_{surface/on}$ is the above surface temperature data and $T_{bath}$ is the temperature of the fluid bathing the catheter.

Figure 13:
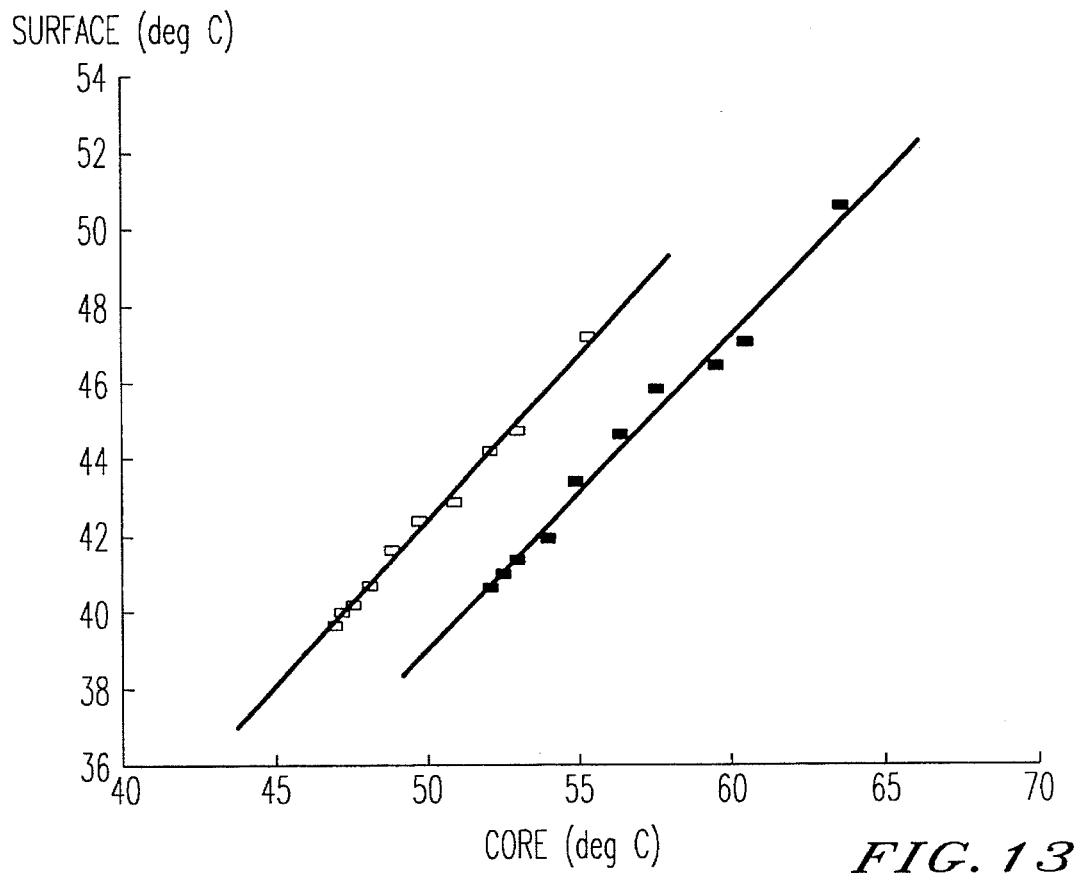
FIG. 13 is a graphical depiction of surface versus core temperature, representing the average of the turbulent and laminar data sets depicted in FIGS. 9–12.

Given that the laminar and turbulent flow cases represent extremes and that in vivo blood flow is highly pulsatile, an average of the two cases is considered an appropriate model of the blood flow around the PA3H catheter in clinical use. FIG. 13 shows the surface temperature versus the corresponding core temperature when the laminar and turbulent data sets are averaged as follows:

$$T_{surface} = [C_{surface} \text{ (laminar)} + T_{surface} \text{ (turbulent)}]/2;$$

and $$T_{core} = [T_{core} \text{ (laminar)} + T_{core} \text{ (turbulent)}]/2$$

These data allow the development of a clinical model for the surface temperature in terms of the measured core temperature and the applied power.

FIG. 13 shows the regression lines for the 10 and 15 watt data sets. Note that the slopes of the two lines are nearly equal, i.e., a temperature versus power slope of approximately 0.85. By assuming the dependence of the regression intercept is linear with respect to power, we can define a linear model for the surface temperature, $T_{surface}$: $T_{surface} = n_{core} * T_{core} + m_{power} * P_{element} + b$, which is, of course, Equation 1. Referring again to FIG. 13, it is apparent that $m_{core}$ is, for this data set, approximately 0.85. Analysis of the regression intercepts (of the lines on FIG. 13 versus power) determines $m_{power}$ as approximately −0.25 (C/watts) and b as approximately 1.1 (C). Equation 1 is thus used by the COC 710, and, specifically, surface temperature calculating unit 728, to estimate the surface temperature of heater elements 400 on a sample by sample basis.

FIGS. 9 and 10 illustrate the heater element core temperature as a function of flow for continuously applied or "constant on" power of 10 and 15 watts. The data in FIG. 9 was taken with the heater element positioned in a turbulent flow region of the test chamber, whereas the element was positioned in a laminar flow region for the data in FIG. 10.

It should be noted that the turbulent and laminar flow cases have equivalent core temperatures are zero flow (approximately 54° and 64° centigrade for 10 and 15 watts), but that the turbulent flow cools the heater element better than the laminar flow and the flow ranges of clinical interest. In general, the core temperature is 5°–8° centigrade warmer at 15 watts power input than at 10 watts, with the largest difference being at zero flow.

The data in FIGS. 9 and 10 were obtained using a standard INTERFLO brand PA3H catheter (heater part number 40245-4001) mounted in a 250 ml test chamber of a temperature controlled flow (37° C.) flow bench. The power to the heater element was from a dc power supply with current and voltage measurements being obtained with standard electronic test equipment. It should also be noted that the "constant on" temperature data represents the peak, not average, core temperatures that would occur with a system according to the preferred embodiment of the invention, since the preferred embodiment pulses the heater over 8/15 of its duty cycle. The method by which the core temperature of heating element 400 is calculated will be demonstrated with reference to the following example:

Example II

A heating element 400 was provided which consisted of a metal foil enclosed by a 0.001 inch layer of Kapton™. It was wrapped around a recessed portion of the catheter, bonded with adhesives and covered with a 0.001 inch thickness of PEVA heat shrink sheath. The metal was selected as a 70% nickel/30% iron alloy in order to provide a high temperature coefficient of electrical resistance (in this specific example, TCR=4200 parts per million per degree centigrade=0.00420 ohm/ohm/centigrade, nominal).

This arrangement allows the temperature of the heater element core, i.e., the metal itself, to be monitored by measuring the electrical resistance of the heater element. The cardiac output computer 710 computes the core temperature, $T_{core}$, as:

$$T_{core} = T_0 + (R - R_0)/(R_0 * TCR); \quad \text{(Equation 1)}$$

Where R is the (time varying) resistance of the heater element 400 and $R_0$ is the reference resistance of the heater element at the reference temperature $T_0$, which in this example is a body temperature of 37° centigrade.

Using this technique, it is estimated that the core temperature $T_{core}$ can be measured to an accuracy of +/−1.3° centigrade. This assumes an error margin for $R_0$ of +/−0.1 ohms; an error for the TCR of +/−0.0001 (1/C); and an error in the reference temperature $T_0$ of +/−0.1° C.

The safety shut-off system within COC 710 further includes a detection unit 730, in communication with the surface temperature calculating unit 728, for determining whether a potential physiologically harmful temperature condition exists at heating element 400. Detection unit 730 is constructed and arranged to instruct a power control unit 740 to cease supplying power to heating element 400 when the calculated surface temperature of heating element 400 exceeds a temperature threshold, defined as:

$$T_{safe\ threshold} = T_{max\ safe}, \text{ if } T_b \text{ is greater or equal to 37° C.,}$$

or $$T_{safe\ threshold} = T_{max\ safe} + (T_b - 37), \text{ otherwise;}$$

where:

$T_b$ is the sample pulmonary artery blood temperature, and $T_{max\ safe}$ is a control parameter.

Referring again to FIG. 15, it will be seen that the detection unit 730 includes a limit comparison subunit 732 having a conditional integrator incorporated therein, and a subunit 734 for comparing a time/temperature product from the conditional integrator to a predetermined maximum value. Detection unit 730 will instruct power unit 740 to cease supplying power to heating element 400 only if $T_{surface}$ exceeds $T_{safe\ threshold}$ for more than a specified integrated time temperature product. The conditional integrator within limit comparison subunit 732 resets to zero when any sample by sample estimate of $T_{surface}$ is below $T_{safe\ threshold}$. Thus, shut-off requires continuous $T_{surface}$ samples above the $T_{safe\ threshold}$ such that their integrated area exceeds a hot area threshold, which is stored in ROM 802. When this occurs, detection unit 730 instructs power control unit 740 to shut-off power to the heating element 400, and the COC 710 exits the operative measurement mode. The time it takes for the integrated $T_{surface}$ to trigger the hot area threshold is a measure of the rate of temperature change in the heater element. If this time is less than a time hot threshold parameter, than the COC 710 considers the catheter to be operating in air, and the message "CHECK HEATER POSITION" appears on an operator warning display unit 736. If the time exceeds the time hot threshold, the catheter is considered to be in the patient, and the message "LOW FLOW DETECTED" appears instead on the operator warning display unit 736.

The values of the safety shut-off parameters used in the current COC 710 are, preferably:

$T_{max\ safe} = 45°$ C.

Hot area threshold=4° C.-seconds

Time hot threshold=0.7 seconds.

$T_{max\ safe}$, the hot area threshold and time hot threshold are also stored in the ROM 802.

2. The Two-State Power Control Method

The temperature dependence of the heater element 400 to blood flow velocity motivates the design of a two state power control method in the COC 710. Based on the flow data exhibited in FIGS. 9 and 10 and the fact that clinical flows are normally above 2.5 lpm, the inventors have endeavored to achieve the following desirable characteristics in the power control method:

1. Initial operation at a power level selected by the initial power selection method described below;

2. When operating at a higher power level, if the flow drops below about 2.5 lpm ($T_{core}$ greater than 56° C. at 15 watts), switch to a lower power level;

3. If, after switching to the lower power level, the flow increases above 3.5 lpm ($T_{core}$ less than 49° C. at 10 watts), switch back to the higher power level.

In the preferred embodiment, the low power level is 10 Watts, and the high power level is 15 Watts. A fourth requirement, which is imposed by the signal processing system according to the preferred embodiment of the invention, required to estimate flow is that a power control unit 738 (shown in FIG. 15) only adjusts the power to the heater at PRBS "run" boundaries.

Figure 14:
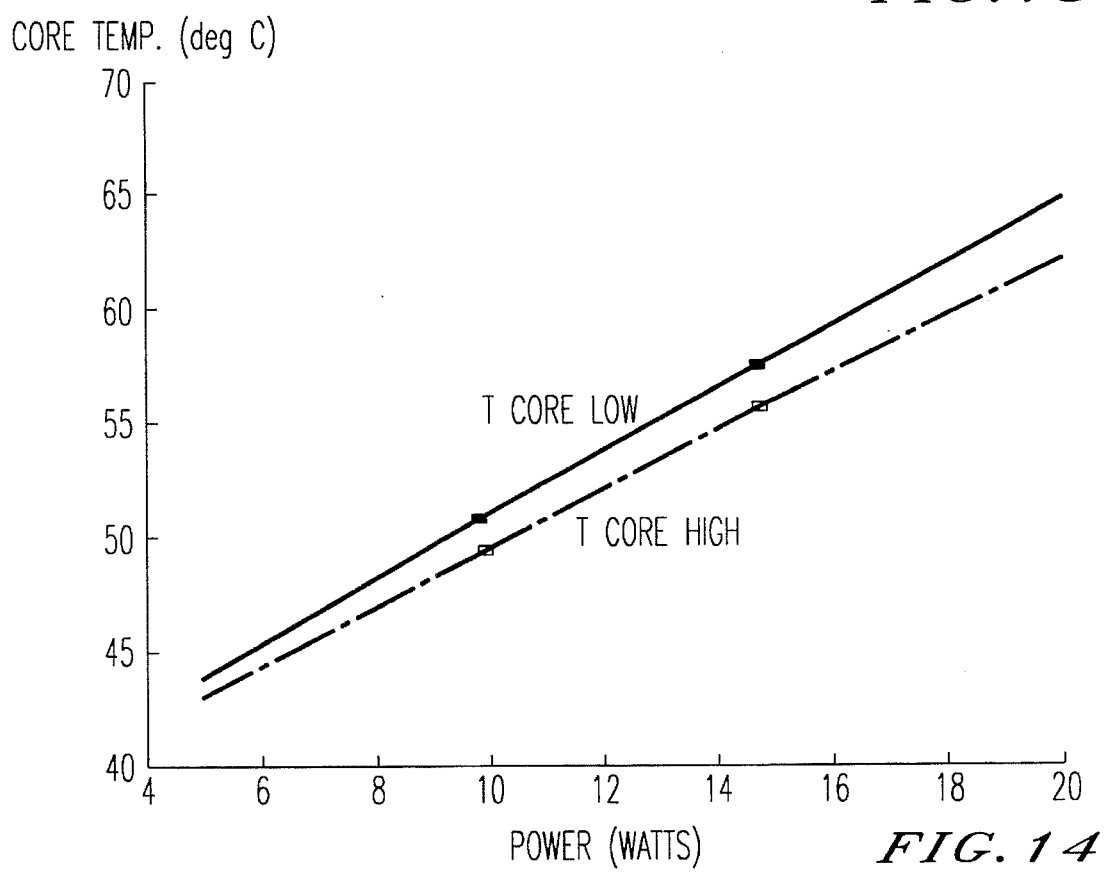
FIG. 14 is a graphical depiction of core temperature versus power for the two state flow dependent power control method according to a preferred embodiment of the invention.

The power control method in the COC 710 compares the measured core temperature to two power dependent core temperature thresholds: $T_{core\ high}$ and $T_{core\ low}$, where "high" and "low" refer to flow, not power. FIG. 14 is a graphical depiction of core temperature versus power for the two thresholds $T_{core\ high}$ and $T_{core\ low}$. As may be seen in the linear depiction of $T_{core\ low}$ and $T_{core\ high}$ in FIG. 14, those thresholds may be calculated as follows:

$$T_{core\ high} = m_{high} * P_{element} + b_{high};$$

and $$T_{core\ low} = m_{low} * P_{element} + b_{low}.$$

Using the data from example 1, upon which the graphical depiction in FIG. 14 is based, $m_{high}$ will have a value of approximately 1.29; $b_{high}$=36.57; $m_{low}$=1.41; and $b_{low}$=36.8.

This comparison is performed on a sample by sample basis during the PRBS run. If either the high or low threshold is exceeded, a corresponding flag is set. If the current power level is 15 watts and the core temperature during the previous run exceeded the $T_{core\ low}$ threshold, the power control unit 738 instructs the power control unit 740 to reduce the power to 10 watts. If the current power level is 10 watts and the core temperature during the previous run did not exceed the $T_{core\ high}$ threshold, the power control unit 738 instructs the power control unit 740 to increase the power back to 15 watts. It should be understood that the invention is not limited to a power control unit which provides power at the disclosed levels and that different power level values could be used, that more than two discrete power levels could be used, and that power could be continuously varied within the scope of the invention.

It should be noted that power control unit 738 thus provides a hysteresis such that slight variations in $T_{core}$ around either threshold do not cause alternate run power switching.

It should be noted that by taking out the power dependence (i.e., making the thresholds a linear function of power), the switching is flow dependent, but independent of the settings for the high and low power states (which are presently 10 and 15 watts). The "*"/"zero" data points in FIG. 14 are the average core temperatures that are obtained at a flow of 1.5/2.5 lpm for approximately 10 and 15 watts. The straight line fits are the $T_{core\ high}$ and $T_{core\ low}$ thresholds versus power. The use of 1.5/2.5 lpm data instead of 2.5/3.5 lpm data is to allow for the effects of core temperature noise.

3. The Heater Resistance Verification System

According to another advantageous feature of the invention, the COC 710 is constructed with an HRV unit 742 so as to be able to determine whether each combination of catheter and instrument passes a safety shut-off verification test. It is actually a system readiness test which is performed upon the initial start of system operation, either after power is on or when the COC 710 recognizes a new catheter.

Figure 16:
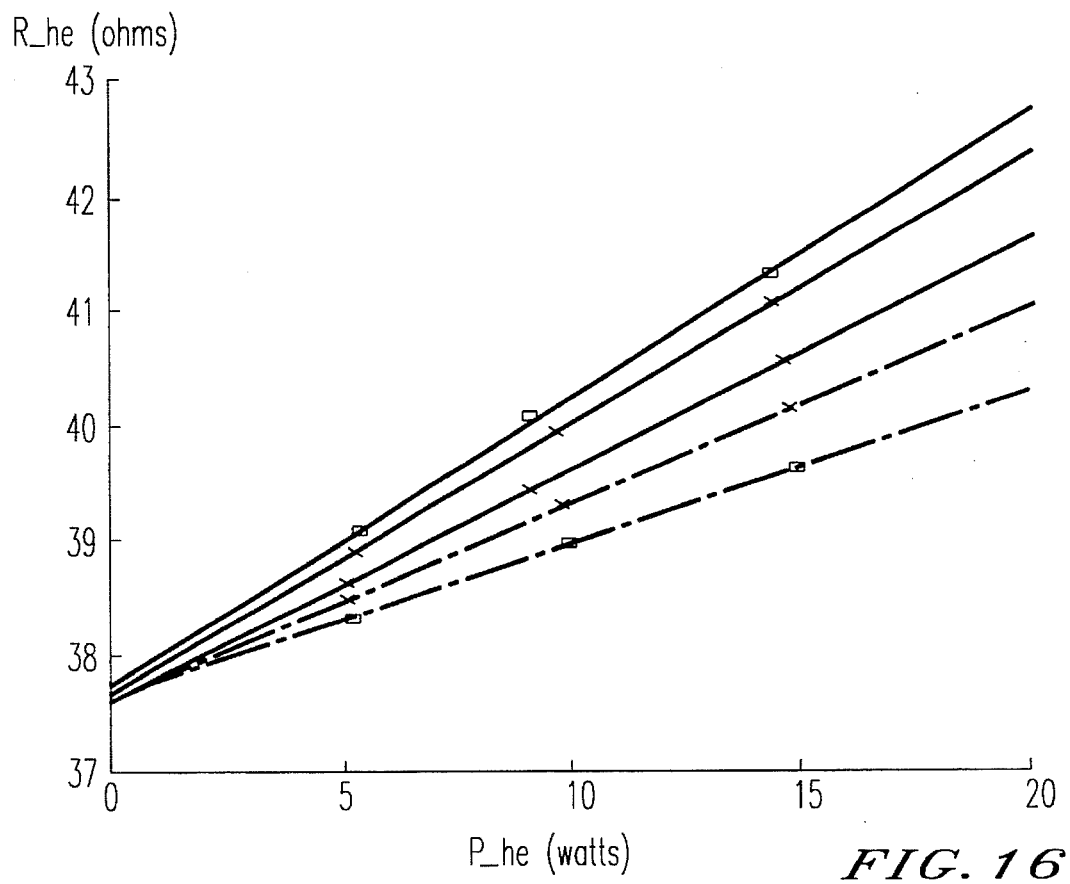
FIG. 16 is a graphical depiction of heater element resistance versus power at constant flows, measured with a dc power supply and test instruments.
Figure 17:
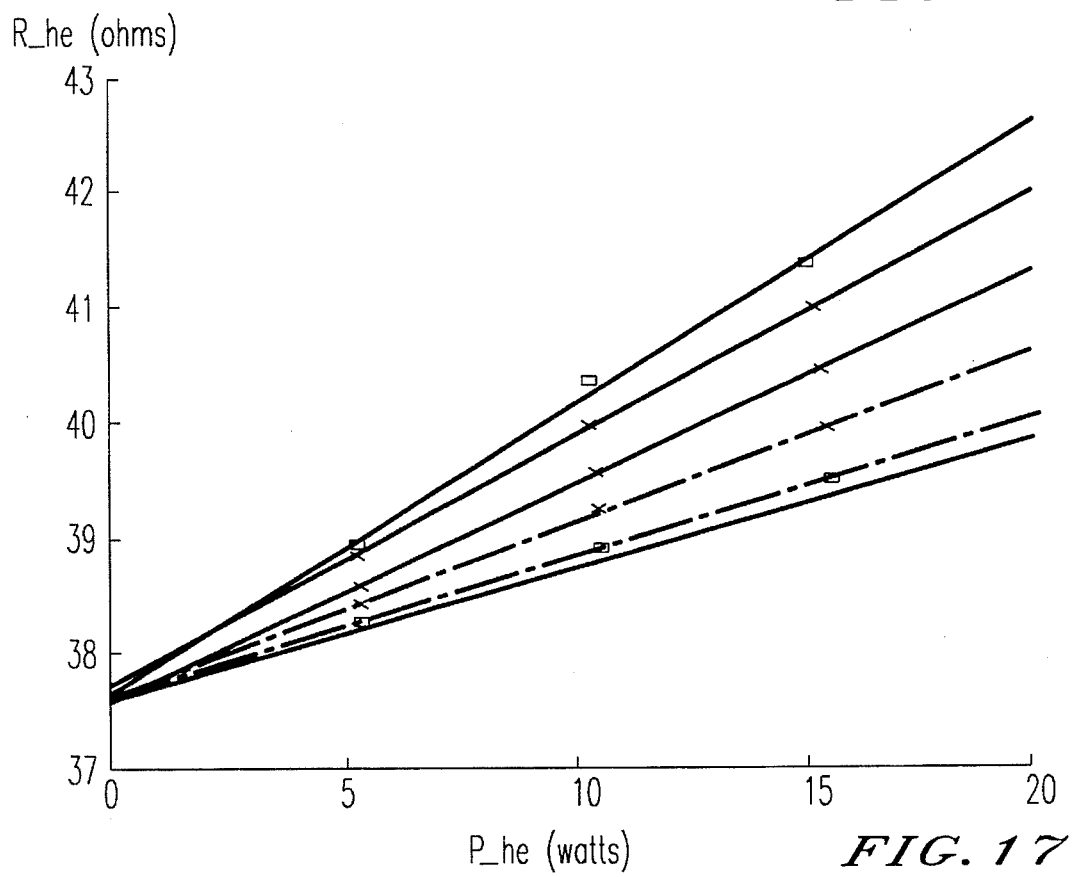
FIG. 17 is a graphical depiction of heat element resistance versus power at constant flows, as estimated by the heater resistance verification system according to a preferred embodiment of the invention.

FIGS. 16 and 17 show data from a feasibility study that illustrates the basic concept of the heater resistance verification system. That concept involves the linear relationship between measured heater resistance and the power applied to the heater element under conditions of constant flow.

Given the fact that flow is constant over the period of measurement, the zero power intercept of the resistance versus power regression line provides a measure of the heater element resistance at the current blood temperature.

The data in FIG. 16 was obtained when the hydromodel catheter was energized with a dc power supply and precision test instruments were used to measure the heater elements current and voltage. The data in FIG. 17 was also obtained with the hydro model catheter, using the COC 710. In both cases, resistance measurements were obtained at power settings of approximately 5, 10, and 15 watts for various constant flows (0, 0.3, 1, 2, 6, and 9 lpm). The measurements were obtained with a continuously applied power allowing 5 seconds or more for the temperature to stabilize after a flow transition.

A straight line was fitted to the data at each flow using the least squares error technique and the resultant slope and intercept data are displayed in the figures. Since the temperature of the bath in the hydro model chamber is controlled to 37+/−0.05° centigrade, the zero power resistance measurement should be equal to the catheter $R_0$ ($T_0$ =37° C.)=37.63 ohms. The results in FIGS. 16 and 17 show the agreement within +/−0.05 ohms, except for the zero flow DC supply measurement, which is within +0.12 ohms. The zero flow bath temperature is the least stable.

The heater resistance verification (or "HRV") algorithm conducted by the HRV unit 742 provides an estimate of Ro from the zero power intercept of the resistance versus power data obtained when the catheter is at the patient's blood temperature. Thus, equation 1 is solved for an estimate of Ro:

$$Ro_b = R_b/[(Tb-To)*TCR+1];$$

where $Ro_b$ is the estimate of the reference resistance Ro;

Rb is the measured zero power resistance intercept;

Tb is the measured blood temperature;

To is the reference bath temperature (stored in ROM 802); and

TCR is the temperature coefficient of resistance (also stored in ROM 802).

The estimate of $RO_b$ is then compared to the catheter reference resistance $R_o$, stored in the ROM 802, and a pass-fail decision is made on whether the calibration of this particular/catheter instrument combination is sufficiently accurate to support the safety shut-off algorithm. A fail decision results in the CCO mode being inactivated and in a message to the operator which advises the use of the injectate mode.

Note that if $Ro_b$ is sufficiently lower than Ro, the safety shut-off algorithm fails to shut-off the instrument under conditions of zero flow, such as when the patient is on bypass. On the other hand, $RO_b$ sufficiently higher than Ro results in the safety shut-off algorithm false triggering at normal levels of cardiac output and in the interruption of measurement mode.

In detail, the HRV algorithm consists of the following steps:

1. Record the blood temperature, $Tb_1$. The blood temperature is measured by the catheter thermistor or thermocouple 104.

2. Activate the heater element to a requested power (which in the preferred embodiment is 5 watts), for a time period (which in the preferred embodiment is 4 seconds) and record the measured heater element resistance and delivered power averaged over the last 2 seconds.

3. Repeat step 2 at a second power level (which in the preferred embodiment is 7.5 watts).

4. Repeat step 2 at a third power level (which in the preferred embodiment is 10 watts).

5. Record the blood temperature again.

6. Validate the data by testing that the absolute value of the difference between the two recorded blood temperatures is less than a maximum threshold value (which in the preferred embodiment is 0.2° centigrade).

7. Use the linear least squares algorithm to compute estimates of (a) the zero power resistance intercept Rb; (b) the uncertainty in the estimate of Rb, $U_{rb}$; (c) the slope of the resistance versus power line, $m_{RP}$; and (d) the uncertainty in the estimate of $m_{RP}$, $U_{mrp}$.

8. Validate the estimates by testing that (a) $U_{rb}$ is less than or equal to $U_{rb\ threshold}$; (b) $m_{RP\ min}$ is less than or equal to $m_{RP}$ is less than or equal to $m_{RP\ max}$; and (c) $U_{mRP}$ is less than or equal to $U_{mRP\ threshold}$, where, in the preferred embodiment, $U_{Rb\ threshold}=0.3$ ohms; $m_{RP\ min}=-0.05$; $m_{RP\ max}=0.5$; and $U_{mRP\ threshold}=0.15$.

9. If the data and/or estimates do not pass the validation tests (steps 6–8) return to step 1. If, after three tries they still fail, 9o to step 12. If they pass validation continue.

10. Using $T_b=0.5*(Tb_1+Tb_2)$ in the To and TCR from the catheter ROM 802, compute $Ro_b$ using Equation 3.

11. Compute $\Delta_{Ro}=Ro-Ro_b$, and test that: $\text{Error}_{Ro\ neg}$ is less than or equal to $\Delta_{Ro}$ if less than or equal to $\text{error}_{Ro\ pos}$, where $\text{error}_{Ro\ neg}$ equals $-1$ ohm and $\text{error}_{Ro\ pos}$ equals $+1$ ohm.

12. If step 11 fails provide the following fault message to the user: "FAULT: CATHETER VERIFICATION ERROR—USE INJECTATE MODE." If step 11 passes, proceed to normal flow measurement operation.

Note that the safety shut-off processing is in effect during the data acquisition phase (steps 2–4) of the HRV processing. Safety shut-off should always have higher priority than HRV.

The initial power selection algorithm performed by the COC 710 will now be described. The regression line obtained from the above HRV algorithm allows the COC 710 to intelligently select the high or low power states (e.g., 15 to 10 watts) for the initial CCO operation. This is done according to the following algorithm:

1. The heater resistance vs power regression line is used to estimate the heater resistance $R_{15}$, at 15 watts, i.e., $$R_{15}=m_{RP}*15+R_b;$$

2. Equation (1) is used to estimate the associated core temperature $T_{core(15)}$, at 15 watts, i.e., $$T_{core(15)}=To+(R_{15}-Ro)/(Ro*TCR);$$

3. Equation (2) is used to estimate the associated surface temperature, $T_{surface(15)}$, at 15 watts, i.e., $$T_{surface(15)}=m_{core}*T_{core(15)}+m_{power(15)}+b;$$

4. $T_{surface(15)}$ is compared to the $T_{max\ safe}$ parameter of the safety shutoff algorithm and the initial power is selected according to:

$T_{max\ safe}$⇒select 10 watts (low state) else⇒select 15 watts (high state).

This procedure for selecting the initial power setting should eliminate the CCO safety shutoff that would otherwise result from initially operating at 15 watts on a patient having a low cardiac output.

It is to be understood, however, that, even though numerous characteristics and advantages of the present invention have been set forth in the foregoing description, together with details of the structure and function of the invention, the disclosure is illustrative only and that changes may be made in detail, especially in matters of shape, size and arrangement of parts within the principles of the invention to the full extent indicated by the broad general meaning of the terms in which the appended claims are expressed.

What is claimed is:

1. A system for keeping a surface temperature of a blood contacting surface of a thermodilution catheter within safe physiological limits, comprising:

a core temperature monitor for monitoring a core temperature of a core of an electric resistance-type thermodilution heater element of the thermodilution catheter;

a power source for supplying electric power to said thermodilution heater element;

a power monitor for monitoring an amount of the electric power that is supplied to said thermodilution heater element;

surface temperature calculating means, in communication with said core temperature monitor and said power monitor, for calculating the surface temperature;

condition determining means, in communication with said surface temperature calculating means, for determining when a potentially physiologically harmful temperature condition exists; and control means, in communication with said core temperature monitor, said power monitor, said power source, and said condition determining means, for controlling the amount of the electric power that is supplied to said thermodilution heater element by said power source, to keep the surface temperature within safe physiological limits;

wherein said condition determining means comprises
  (i) means for detecting when the surface temperature exceeds a predetermined physiologically safe temperature limit, and
  (ii) time-temperature product determining means, for determining a time-temperature product of (1) time during which the surface temperature is above the predetermined physiologically safe temperature limit and (2) extent to which the surface temperature exceeds the predetermined physiologically safe temperature limit,
  (iii) a time based integrator for collecting and storing the time-temperature product; and
  (iv) means, in communication with said time based integrator, for comparing the time-temperature product to a predetermined maximum time-temperature value; and the system further comprising condition indicating means, in communication with said condition determining means, for indicating when the time-temperature product exceeds the predetermined maximum time-temperature value.

2. A system according to claim 1, wherein said control means is in communication with said time-temperature product determining means and comprises means for reducing the amount of the electric power delivered to said thermodilution heater element when said condition indicating means indicates that the time-temperature product has exceeded the predetermined maximum time-temperature value.

3. A system according to claim 1, wherein the condition determining means further comprises time measuring means for measuring the amount of time that is taken for the time-temperature product to exceed the predetermined maximum value; and the system further comprises means for warning an operator to check the position of said thermodilution catheter if the amount of time measured by the time measuring means is less than a predetermined minimum value.

4. A system according to claim 1, wherein the condition determining means further comprises means for measuring the amount of time that is taken for the time-temperature product to exceed the predetermined maximum value; and the system further comprises means for warning an operator that a low flow situation exists if the amount of time measured by the means for measuring the amount of time that is taken for the time-temperature product to exceed the predetermined maximum value is less than a predetermined minimum value.

5. A system according to claim 1, further comprising a resistance monitor which is adapted for communication with said heater element and said core temperature monitor, for monitoring the electrical resistance of said thermodilution heater element.

6. A system according to claim 5, wherein said core temperature monitor comprises a core temperature calculating means for calculating the core temperature of said thermodilution heater element as a function of its electrical resistance determined by said resistance monitor.

7. A system according to claim 6, wherein core temperature calculating means functions to calculate the core temperature based on:

(a) a reference resistance at a reference temperature; and (b) a temperature coefficient of electrical resistance of said thermodilution heater element.

8. A system according to claim 7, wherein said core temperature calculating means further functions to calculate the ore temperature according to the formula:

$$T_{core} = T_0 + (R - R_0)/(R_0 * TCR);$$

where $T_{core}$ is the core temperature; $T_0$ is the reference temperature; R is said thermodilution heater element resistance measured by said resistance monitor; $R_0$ is the reference resistance; and TCR is the temperature coefficient of electrical resistance of said thermodilution heater element.

9. A system according to claim 5, further comprising means for measuring voltage and current that are supplied to said thermodilution heater element and wherein said resistance monitor comprises means, in communication with said means for measuring, for calculating the electrical resistance of said thermodilution heater element based on the voltage and current that are measured by said means for measuring.

10. A system according to claim 1, further comprising means for measuring voltage and current that are supplied to said thermodilution heater element and wherein said power monitor comprises means, in communication with said means for measuring, for calculating the amount of the electric power that is delivered to said thermodilution heater element based on voltage and current that are measured by said means for measuring.

11. A system according to claim 1, wherein the control means comprises means for reducing the amount of the electric power delivered to said thermodilution heater element when the surface temperature exceeds the safe physiological temperature limits.

12. A system according to claim 11, wherein said surface temperature calculating means functions to calculate the surface temperature based on factors which comprise values for:

(a) the core temperature;

(b) the electric power that is delivered to said thermodilution heating element; and (c) information that has been empirically determined for said thermodilution catheter under anticipated clinical conditions.

13. A system according to claim 11, wherein said surface temperature calculating means further functions to calculate the surface temperature according to the formula:

$$T_{surface} = m_{core} * T_{core} + m_{power} * P_{element} + b;$$

where $T_{surface}$ is the surface temperature, $m_{core}$ is a constant relating the core temperature to the surface temperature under anticipated clinical conditions; $T_{core}$ is the core temperature; $m_{power}$ is a constant relating the power delivered to said thermodilution heater element to the incremental increases in the surface temperature that will be created by the power under anticipated clinical conditions; $P_{element}$ is the amount of the electric power that is delivered to said thermodilution heater element; and b is a numerical constant.

14. A system for keeping a surface temperature of a blood contacting surface of a thermodilution catheter within safe physiological limits, comprising:

a core temperature monitor for monitoring a core temperature of a core of an electric resistance-type thermodilution heater element of said thermodilution catheter;

a power source for supplying electric power to said thermodilution heater element;

a power monitor for monitoring the amount of electric power that is supplied to said thermodilution heater element; and control means, in communication with said core temperature monitor and with said power monitor, for controlling the amount of the electric power that is supplied to said thermodilution heater element by said power source to maintain the surface temperature within safe physiological limits;

wherein said power source comprises means for supplying power at, electively, either a first fixed power level or a second fixed power level which is greater than the first fixed power level; and said control means controls whether said power source supplies power at the first fixed power level or the second fixed power level.

15. A system according to claim 14, wherein said control means is configured to function such that:

(a) when power is being supplied from said power source to said thermodilution heater element at the first fixed power level, said control means instructs said power source to begin supplying power at the second fixed power level when the core temperature monitored by said core temperature monitor is equal to or less than a first predetermined temperature value; and (b) when power is being supplied from said power source to said thermodilution heater element at the second fixed power level, said control means instructs said power source to begin supplying power at the first fixed power level when the core temperature monitored by said core temperature monitor is equal to or greater than a second predetermined temperature value; and (c) the first predetermined temperature value is less than the second predetermined temperature value.

16. A system according to claim 15, wherein, during start-up of the system, said control means functions select either the first power level or the second power level.

17. A method for keeping a surface temperature of a blood contacting surface of a thermodilution catheter within safe physiological limits, comprising the steps of:

(a) monitoring a core temperature of a core of an electric resistance-type thermodilution heater element of said thermodilution catheter;

(b) supplying electric power to said thermodilution heater element;

(c) monitoring the amount of electric power that is supplied to said thermodilution heater element;

(d) calculating the surface temperature, based at least in part on the core temperature and the amount of the electric power that is supplied to the thermodilution heater element;

(e) determining, based at least in part on the surface temperature, whether a potentially physiologically harmful temperature condition exists; and (f) controlling the amount of the electric power that is supplied to said thermodilution heater element to keep the surface temperature within safe physiological limits;

wherein step (e) comprises the steps of:

(i) collecting and storing a time-temperature integration product based on the extent to which surface temperature exceeds a predetermined safe temperature limit; and (ii) comparing the time-temperature product to a predetermined maximum time-temperature value.

18. A method according to claim 17, further comprising the step of reducing the amount of the electrical power that is supplied to said thermodilution heater element when the time-temperature integration product exceeds the predetermined maximum time-temperature value.

19. A method according to claim 17, wherein step (e) further comprises measuring the amount of time that is taken for the time-temperature integration product to exceed the predetermined maximum time-temperature value; and said method further comprising the step of warning an operator to check the position of said thermodilution catheter if the amount of time that is measured for the time-temperature integration product to exceed the predetermined maximum value is less than a predetermined minimum time value.

20. A method according to claim 17, wherein step (e) further comprises measuring the amount of time that is taken for the time-temperature integration product to exceed the predetermined maximum time-temperature value; and said method further comprising the step of warning an operator that a low flow situation exists if the amount of time that is measured for the time temperature integration product to exceed the predetermined maximum time-temperature value is less than a predetermined minimum time value.

21. A method for keeping a surface temperature of a blood contacting surface of a thermodilution catheter within safe physiological limits, comprising:

(a) monitoring a core temperature of a core of an electric resistance-type thermodilution heater element of said thermodilution catheter;

(b) supplying electric power to said thermodilution heater element;

(c) monitoring an amount of the electric power that is supplied to said thermodilution heater element by said power source;

(d) controlling the amount of the electric power that is supplied to said thermodilution heater element based on the core temperature so that the surface temperature is kept within safe physiological limits;

wherein step (d) is performed by alternating the amount of the electrical power that is supplied to said thermodilution heater element between a first fixed power level and a second fixed power level which is greater than the first fixed power level.

22. A method for keeping a surface temperature of a blood contacting surface of a thermodilution catheter within safe physiological limits, comprising:

(a) monitoring a core temperature of a core of an electric resistance-type thermodilution heater element of said thermodilution catheter;

(b) supplying electric power to said thermodilution heater element;

(c) monitoring an amount of the electric power that is supplied to said thermodilution heater element;

(d) controlling the amount of the electric power that is supplied to said thermodilution heater element based on the core temperature so that the surface temperature is kept within safe physiological limits;

wherein step (d) is further performed by:

(i) when the electric power is being supplied at a first power level, increasing the electric power to second power level when the core temperature is equal to or less than a first predetermined temperature value; and (ii) when the electric power is being supplied at the second power level, decreasing the electric power to the first power level when the core temperature is equal to or greater than a second predetermined temperature value; and (iii) wherein the first predetermined temperature value is less than the second predetermined temperature value.

23. A system for keeping a surface temperature of a blood contacting surface of a thermodilution catheter within safe physiological limits, comprising:

a core temperature monitor for monitoring a core temperature of a core of an electric resistance-type thermodilution heater element of the thermodilution catheter;

a power source for supplying electric power to said thermodilution heater element;

a power monitor for monitoring an amount of the electric power that is supplied to said thermodilution heater element;

surface temperature calculating means, in communication with said core temperature monitor and said power monitor, for calculating the surface temperature;

condition determining means, in communication with said surface temperature calculating means, for determining when a potentially physiologically harmful temperature condition exists;

control means, in communication with said core temperature monitors, said power monitor, said power source, and said condition determining means, for controlling the amount of the electric power that is supplied to said thermodilution heater element by said power source, to keep the surface temperature within safe physiological limits; wherein said condition determining means comprises means for determining when the surface temperature exceeds a predetermined physiologically safe temperature limit; and further comprising means, in communication with said determining means, for warning an operator to check the position of said thermodilution catheter when the surface temperature exceeds the predetermined safe physiological temperature limit.

* * * * *